United States Patent [19]
Nagata et al.

[11] Patent Number: 6,030,746
[45] Date of Patent: Feb. 29, 2000

[54] DI- AND TRIPHENYL MONOTERPENE HYDROCARBON DERIVATIVES, DISSOLUTION INHIBITORS, AND CHEMICALLY AMPLIFIED POSITIVE RESIST COMPOSITIONS

[75] Inventors: Takeshi Nagata; Satoshi Watanabe; Tsunehiro Nishi; Jun Hatakeyama; Shigehiro Nagura; Toshinobu Ishihara, all of Nakakubiki-gun, Japan

[73] Assignee: Shin-Etsu Chemical Co., Ltd., Tokyo, Japan

[21] Appl. No.: 08/831,749

[22] Filed: Apr. 1, 1997

[30] Foreign Application Priority Data

Apr. 10, 1996 [JP] Japan .................................. 8-113197

[51] Int. Cl.[7] .......................... G03F 7/004; C07C 43/30
[52] U.S. Cl. ...................... 430/270.1; 430/917; 568/591; 568/592; 568/631; 568/632; 568/633; 568/644
[58] Field of Search .............................. 430/270.1, 917; 568/591, 592, 631, 633, 632, 644

[56] References Cited

U.S. PATENT DOCUMENTS 5,824,451 10/1998 Aoai et al. ............................ 430/270.1

Primary Examiner—John S. Chu
Attorney, Agent, or Firm—Millen, White, Zelano & Branigan, P.C.

[57] ABSTRACT

Di- or triphenyl monoterpene hydrocarbon derivatives of formula (1) are novel.

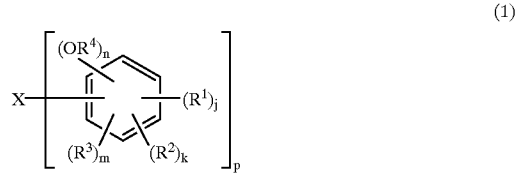

(1)

X is a di- or trivalent monoterpene hydrocarbon group, $R^1$ to $R^3$ are hydrogen or an alkyl, alkoxy, alkoxyalkyl, alkenyl or aryl group, $R^4$ is hydrogen or an acid labile group, at least one $R^4$ being an acid labile group, letter n is an integer of 1–5, j, k and m are integers of 0–4, n+j+k+m=5, and p is 2 or 3. When used as a dissolution rate regulator, the compound of formula (1) exerts remarkably enhanced dissolution inhibitory effect and minimized light absorption in the deep-UV region. A chemically amplified positive resist composition having the compound of formula (1) blended therein is highly sensitive to actinic radiation such as deep-UV radiation, electron beam and X-ray, especially KrF excimer laser light, and has improved sensitivity, resolution and plasma etching resistance.

30 Claims, No Drawings

DI- AND TRIPHENYL MONOTERPENE HYDROCARBON DERIVATIVES, DISSOLUTION INHIBITORS, AND CHEMICALLY AMPLIFIED POSITIVE RESIST COMPOSITIONS

BACKGROUND OF THE INVENTION

1. Field of the Invention

This invention relates to a novel di- or triphenyl monoterpene hydrocarbon derivative useful as a dissolution rate regulator and a chemically amplified positive resist composition containing the same and suitable for use in fine patterning.

2. Prior Art

As the LSI technology tends toward higher integration and higher speed, further refinement of pattern rules is required. The current patterning technology mostly relies on light exposure which is now approaching to the essential limit of resolution which is dictated by the wavelength of a light source. It is generally recognized that in light exposure using g-line (wavelength 436 nm) or i-line (wavelength 365 nm) as a light source, a pattern rule of about 0.5 μm is the limit. For LSIs fabricated by such light exposure technique, a degree of integration equivalent to 16 mega-bit DRAM is the limit. At present, LSIs fabricated in the laboratory have reached this stage. It is urgently required to develop a finer patterning technique.

Under such circumstances, deep-ultraviolet lithography is regarded promising as the next generation of fine patterning technology. The deep-UV lithography is capable of working on the order of 0.3 or 0.4 μm and makes it possible to form a resist pattern having a side wall nearly perpendicular to the substrate if a less light absorbing resist material is used. Advanced engineers place focus on the utilization of high illuminance KrF excimer laser as a deep-UV source. A resist material having low light absorption and high sensitivity must be developed before such an excimer laser can be used in a mass scale manufacturing technique.

From this point of view, a number of chemically amplified positive working resist materials using acid catalysts were recently developed as disclosed in JP-B 27660/1990, JP-A 27829/1988, U.S. Pat. Nos. 4,491,628 and 5,310,619. These materials have high sensitivity, resolution and dry etching resistance and are promising as resist materials especially suited for deep-UV lithography.

It is known that the function of chemically amplified positive resist material is largely governed by a dissolution rate regulator or inhibitor used therein. There are known a number of dissolution inhibitors while those having enhanced dissolution inhibiting ability are (i) compounds having at least two acid labile groups wherein the acid labile groups at the remotest positions are intervened by at least 10 linking atoms excluding the acid labile groups and (ii) compounds having at least three acid labile groups wherein the acid labile groups at the remotest positions are intervened by at least 9 linking atoms excluding the acid labile groups as disclosed in JP-A 266109/1994. Exemplary such compounds are shown below by formulae (3a) and (3b).

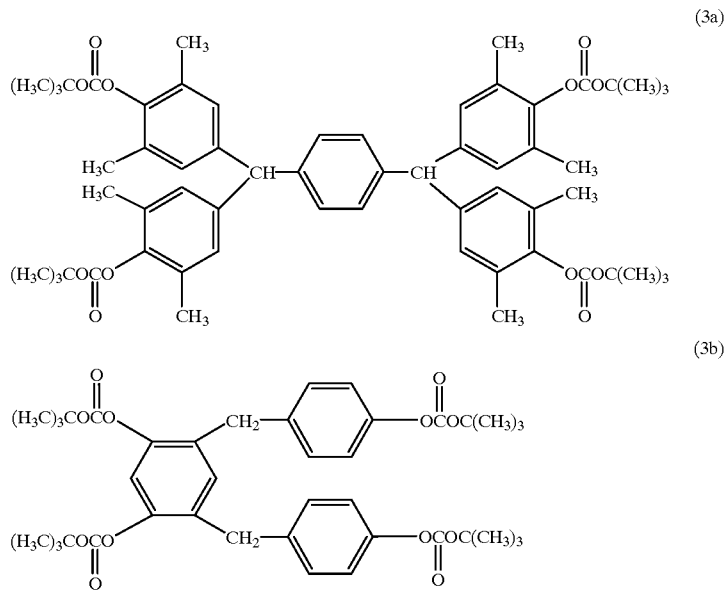

The aforementioned compounds themselves are lipophilic and have the above-mentioned properties. When blended as a resist component, a dissolution inhibitor of this type acts to reduce the solubility of the resist material in aqueous alkali solution thus preventing the resist film from thinning upon development. In exposed areas, an acid is generated to eliminate the acid labile group from the dissolution inhibitor so that the exposed areas become soluble in aqueous alkali solution. In this way, the same dissolution inhibitor acts to increase the dissolution rate of exposed areas.

However, chemically amplified positive resist compositions using the aforementioned compounds as a dissolution rate regulator fail to provide high resolution upon alkali development. This is probably because the compounds have greater light absorption in the deep-UV region. When a chemically amplified positive resist composition containing the same is used in deep-UV lithography, it is difficult to form a pattern having a side wall perpendicular to the substrate. As a consequence, high resolution is not expected. An improvement in this respect is thus desired.

SUMMARY OF THE INVENTION

Therefore, a primary object of the present invention is to provide a novel di- or triphenyl monoterpene hydrocarbon derivative-which is suitable as one component of a chemically amplified positive resist composition. Another object is to provide an improved dissolution rate regulator. A further object is to provide a chemically amplified positive resist composition containing the derivative as a dissolution rate regulator and suitable for use in fine patterning.

We have found that a novel di- or triphenyl monoterpene hydrocarbon derivative of the following general formula (1) has improved properties required for a dissolution rate regulator and is thus suitable as one component of a chemically amplified positive resist composition which has high resolution enough to comply with a fine processing technique and is especially advantageous in deep-UV lithography.

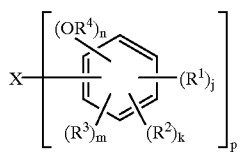
(1)

In formula (1), X is a divalent or trivalent monoterpene hydrocarbon group, $R^1$ to $R^3$ are independently a hydrogen atom, normal or branched alkyl, normal or branched alkoxy, normal or branched alkoxyalkyl, normal or branched alkenyl or aryl group, $R^4$ is a hydrogen atom or acid labile group, preferably an acid labile group of formula (2a), (2b), (2c) or (2d), at least one $R^4$ being an acid labile group, letter n is an integer of 1 to 5, letters j, k and m are integers of 0 to 4 and satisfy n+j+k+m=5, and p is equal to 2 or 3.

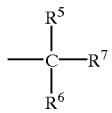
(2a)

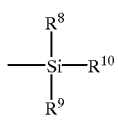
(2b)

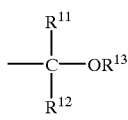
(2c)

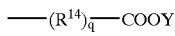
(2d)

$R^5$ to $R^{10}$ are independently a normal or branched alkyl, normal or branched alkoxy, normal or branched alkoxyalkyl, normal or branched alkenyl or aryl group, which may contain a carbonyl group in their chain. Alternatively, $R^5$ and $R^6$, and $R^8$ and $R^9$, taken together, may form a ring. $R^{11}$ and $R^{12}$ are independently a hydrogen atom, normal or branched alkyl, normal or branched alkoxy, normal or branched alkoxyalkyl, normal or branched alkenyl or aryl group. $R^{13}$ is a normal or branched alkyl, normal or branched alkoxyalkyl, normal or branched alkenyl or aryl group, which may contain a carbonyl group in their chain. Alternatively, $R^{13}$ may form a ring with $R^{12}$. $R^{14}$ is a divalent aliphatic, alicyclic or aromatic group. Y is an acid labile group. Letter q is equal to 0 or 1.

Where at least one derivative of formula (1), preferably a mixture of derivatives of formula (1) wherein 10 to 100 mol % of the entire $R^4$ groups is an acid labile group is used as a dissolution rate regulator of a chemically amplified positive resist composition, this dissolution rate regulator exerts enhanced dissolution inhibitory effect prior to acidolysis, providing an increased dissolution contrast. In addition, since this dissolution rate regulator has low light absorption in the deep-UV region, the chemically amplified positive resist composition is free from degradation of a pattern profile and a drop of resolution when applied to deep-UV lithography. Therefore, the novel derivative of formula (1) exerts its function to the full extent particularly when it is used as a dissolution rate regulator of a chemically amplified positive resist composition, from which a resist image featuring high resolution and a wide range of focal depth is obtainable.

It is noted that those compounds of formula (1) wherein all —$OR^4$ groups are phenolic hydroxyl groups are already disclosed in JP-A 261381/1995. When these compounds are used as a dissolution rate regulator, the resulting chemically amplified positive resist composition is less satisfactory with respect to resolution, pattern profile, and focal depth.

Therefore, in a first aspect, the present invention provides a di- or triphenylmonoterpene hydrocarbon derivative of formula (1). In one preferred embodiment, the acid labile group represented by $R^4$ in formula (1) is a group of the general formula (2a), a silyl group of the general formula (2b), an acetal group of the general formula (2c) or a group of the general formula (2d). Also contemplated herein is a mixture of derivatives of formula (1) wherein 10 to 100 mol % of the entire $R^4$ groups being an acid labile group.

In a second aspect, the invention provides a dissolution rate regulator comprising at least one derivative of formula (1).

In a third aspect, the invention provides a chemically amplified positive resist composition comprising a dissolution rate regulator in the form of a derivative of formula (1). More specifically, the chemically amplified positive resist composition is defined as comprising (A) an organic solvent, (B) an alkali soluble resin, (C) a photoacid generator, (D) a dissolution rate regulator in the form of a derivative of formula (1), and optionally, (E) another dissolution rate regulator.

DESCRIPTION OF THE PREFERRED EMBODIMENTS

Novel di- and triphenylmonoterpene hydrocarbon derivatives according to the present invention are of the following general formula (1).

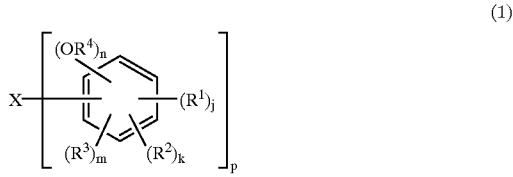
(1)

In formula (1), X is a divalent or trivalent monoterpene hydrocarbon group. Any desired one may be selected from di- and trivalent monoterpene hydrocarbon groups which are derived from non-cyclic or monocyclic monoterpenes. Preferred examples of the non-cyclic monoterpene include myrcene, ocimene, geraniol, and nerol. Preferred examples of the monocyclic monoterpene include limonene, terpinene, sylvestrene, and phellandrene.

$R^1$ to $R^3$ are independently a hydrogen atom, normal or branched alkyl, normal or branched alkoxy, normal or branched alkoxyalkyl, normal or branched alkenyl or aryl group. Exemplary alkyl groups are those having 1 to 10 carbon atoms, such as methyl, ethyl, propyl, isopropyl, n-butyl, sec-butyl, tert-butyl, hexyl, cyclohexyl, and adamantyl groups, with the methyl, ethyl, isopropyl, and tert-butyl groups being preferred. Exemplary alkoxy groups are those having 1 to 8 carbon atoms, such as methoxy, ethoxy, propoxy, isopropoxy, n-butoxy, sec-butoxy, tert-butoxy, hexyloxy, and cyclohexyloxy groups, with the methoxy, ethoxy, isopropoxy, and tert-butoxy groups being preferred. Exemplary alkoxyalkyl groups are those having 2 to 10 carbon atoms, such as methoxymethyl, ethoxypropyl, propoxyethyl, and tert-butoxyethyl groups, with the methoxymethyl, methoxyethyl, ethoxypropyl, and propoxyethyl groups being preferred. Exemplary alkenyl groups are those having 2 to 4 carbon atoms, such as vinyl, propenyl, allyl, and butenyl groups. Exemplary aryl groups are those having 6 to 14 carbon atoms, such as phenyl, xylyl, toluyl, and cumenyl groups.

$R^4$ is a hydrogen atom or acid labile group. At least one $R^4$ must be an acid labile group. Preferably, 10 to 100 mol %, especially 30 to 100 mol % of the entire $R^4$ groups is an acid labile group. The term "acid labile group" means that an acidic functional group such as a phenolic hydroxyl group and carboxyl group is replaced by at least one functional group which is decomposable in the presence of an acid. Any desired acid labile group may be used insofar as it can be decomposed in the presence of an acid to liberate a functional group exhibiting alkali solubility. Preferably, the acid labile group is of the following general formula (2a), (2b), (2c) or (2d).

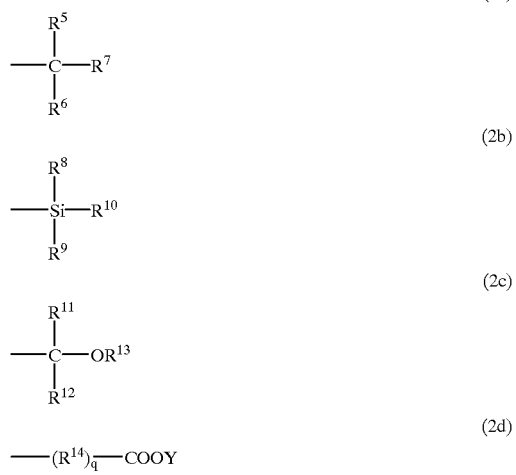

In the formulae, $R^5$ to $R^{10}$ are independently a normal or branched alkyl, normal or branched alkoxy, normal or branched alkoxyalkyl, normal or branched alkenyl or aryl group, which may contain a carbonyl group in their chain. Alternatively, $R^5$ and $R^6$, and $R^8$ and $R^9$, taken together, may form a ring. $R^{11}$ and $R^{12}$ are independently a hydrogen atom, normal or branched alkyl, normal or branched alkoxy, normal or branched alkoxyalkyl, normal or branched alkenyl or aryl group. $R^{13}$ is a normal or branched alkyl, normal or branched alkoxyalkyl, normal or branched alkenyl or aryl group, which may contain a carbonyl group in their chain. Alternatively, $R^{12}$ and $R^{13}$, taken together, may form a ring. $R^{14}$ is a divalent aliphatic, alicyclic or aromatic group. Y is an acid labile group. Letter q is equal to 0 or 1.

Examples of the alkyl, alkoxy, alkoxyalkyl, alkenyl and aryl groups represented by $R^5$ to $R^{13}$ are the same as exemplified for $R^1$ to $R^3$. Examples of the ring that $R^5$ forms with $R^6$ include those rings having 4 to 10 carbon atoms, such as cyclohexylidene, cyclopentylidene, 3-oxocyclohexylidene, and 4-methylcyclohexylidene groups.

Examples of the ring that $R^8$ forms with $R^9$ include those rings having 3 to 9 carbon atoms, such as 1-silacyclohexylidene, 1-silacyclopentylidene, 3-oxo-1-silacyclopentylidene, and 4-methyl-1-silacyclopentylidene groups.

Examples of the ring that $R^{12}$ forms with $R^{13}$ include those rings having 4 to 10 carbon atoms, such as 2-oxacyclohexylidene, 2-oxacyclopentylidene, and 2-oxa-4-methylcyclohexylidene groups.

Examples of the divalent aliphatic group represented by $R^{14}$ include those groups having 1 to 8 carbon atoms, such as methylene, ethylene, propylene, butylene, 2-methylpropylene, and 2-methyl-3-ethoxybutylene groups, with the methylene, ethylene, and propylene groups being preferred. Examples of the divalent alicyclic group represented by $R^{14}$ include those groups having 5 to 10 carbon atoms, such as cyclohexylene. Examples of the divalent aromatic group represented by $R^{14}$ include those groups having 6 to 14 carbon atoms, such as phenylene, xylylene, toluylene, cumenylene groups.

Examples of the acid labile group represented by Y include the groups of formulae (2a), (2b) and (2c).

Examples of the group of formula (2a) include tertiary alkyl groups having 4 to 10 carbon atoms, such as tert-butyl, 1,1-dimethylpropyl, 1,1-dimethylbutyl, 1-ethyl-1-methylpropyl, and 1,1-diethylpropyl groups as well as 3-oxyalkyl groups such as 3-oxocyclohexyl.

Examples of the group of formula (2b) include trialkylsilyl groups having 3 to 10 carbon atoms, such as trimethylsilyl, ethyldimethylsilyl, dimethylpropylsilyl, diethylmethylsilyl, and triethylsilyl groups.

Examples of the group of formula (2c) include those groups having 2 to 8 carbon atoms, such as 1-methoxymethyl, 1-methoxyethyl, 1-ethoxyethyl, 1-n-propoxyethyl, 1-tert-butoxyethyl, 1-n-butoxyethyl, 1-1-butoxyethyl, 1-tert-pentoxyethyl, 1-cyclohexyloxyethyl, 1-(2'-n-butoxyethoxy)ethyl, 1-(2'-ethylhexyl)oxyethyl, 1-(4'-acetoxymethylcyclohexylmethyloxy)ethyl, 1-{4'-(tert-butoxycarbonyloxymethyl)cyclohexylmethyloxy}ethyl, 2-methoxy-2-propyl, 1-ethoxypropyl, dimethoxymethyl, diethoxymethyl, tetrahydrofuranyl, and tetrahydropyranyl groups.

Examples of the group of formula (2d) include tert-butoxycarbonyl, trimethylsilyloxycarbonyl, methoxymethoxycarbonyl, tetrahydropyranyloxycarbonyl, tert-butoxycarbonylmethyl, trimethylsilyloxycarbonylmethyl, methoxymethoxycarbonylmethyl, 1-ethoxyethoxycarbonylmethyl, tetrahydropyranyloxycarbonylmethyl, tetrahydrofuranyloxycarbonylmethyl, tert-butoxycarbonylethyl, 4-tert-butoxycarbonylphenyl, 1-tertbutoxycarbonylcyclohexyl, and 4-tert-butoxycarbonylcyclohexyl groups.

Referring to formula (1) again, letter n is an integer of 1 to 5, preferably 1 to 3, letters j, k and m are integers of 0 to 4 and satisfy n+j+k+m 5, and p is equal to 2 or 3.

Preferred examples of the compound of formula (1) are phenols of the following general formulae (4a) to (4d).

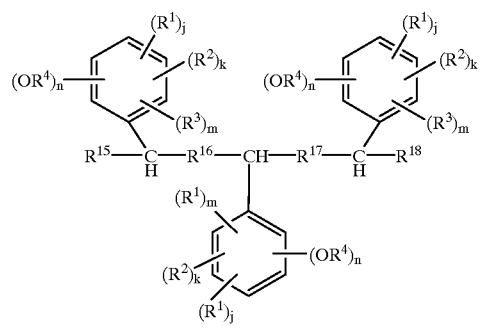
(4a)

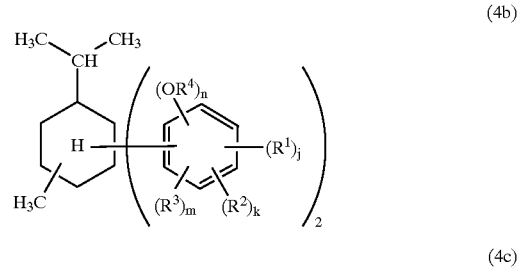
(4b)

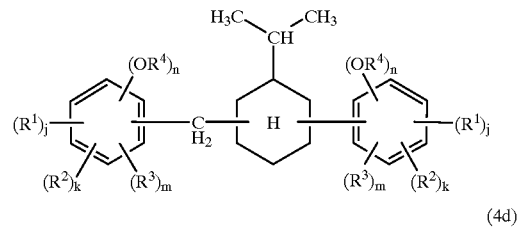
(4c)

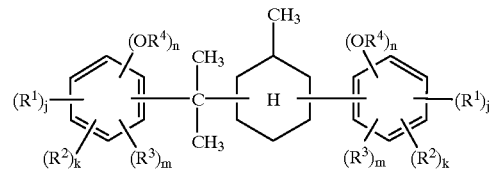
(4d)

In formula (4a), $R^{15}$ and $R^{18}$ each are a normal or branched alkyl group and $R^{16}$ and $R^{17}$ each are a normal or branched alkylene group while the total number of carbon atoms in $R^{15}$ to $R^{18}$ is 7.

More illustrative examples of the compound of formula (1) include compounds of the following formulae (5a) to (5o).

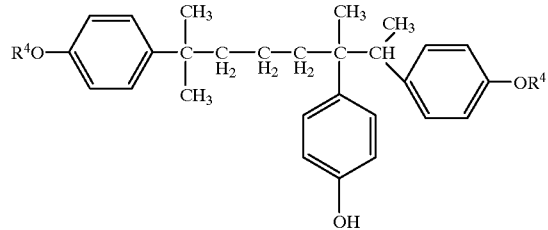
(5a)

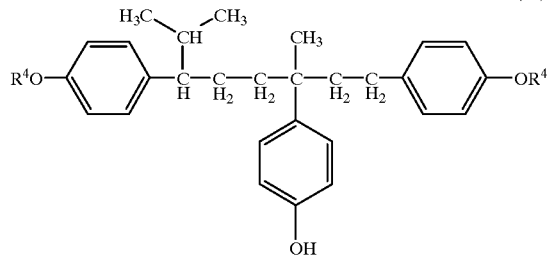
(5b)

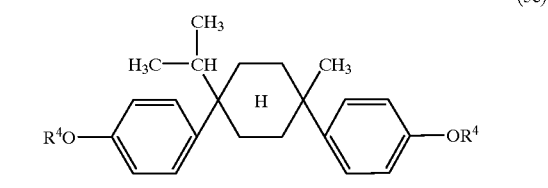
(5c)

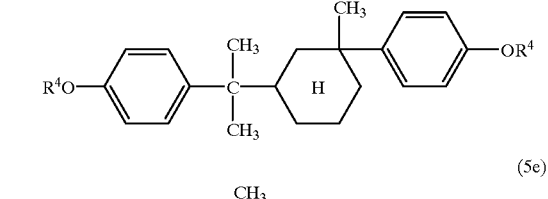
(5d)

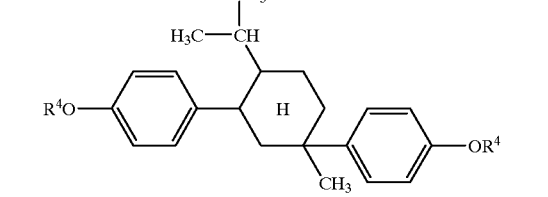
(5e)

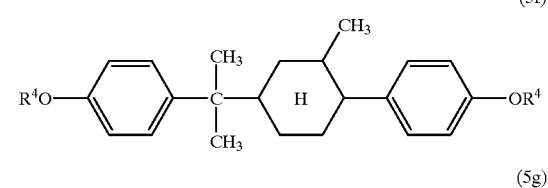
(5f)

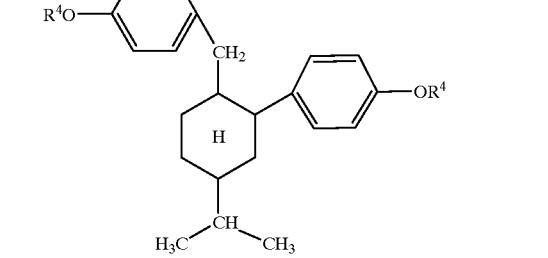
(5g)

(5h)
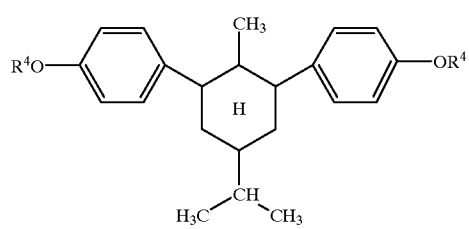

(5i)
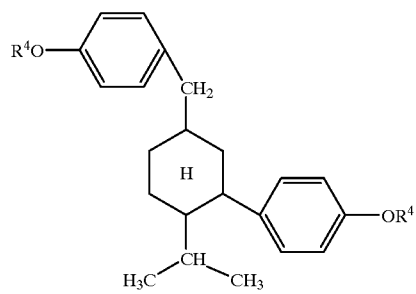

(5j)
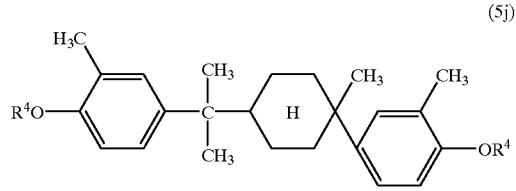

(5k)
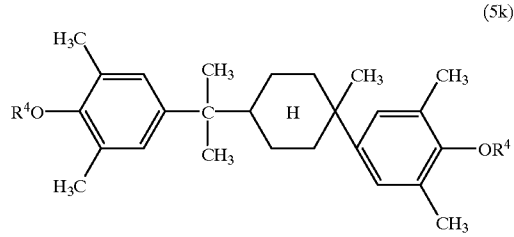

(5l)
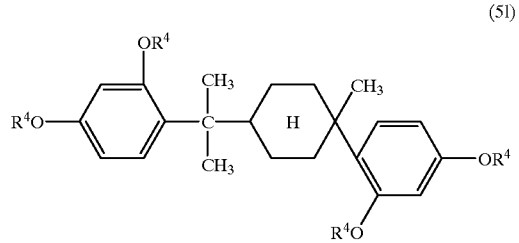

(5m)
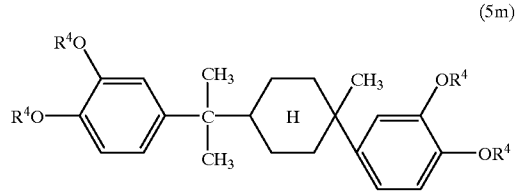

(5n)
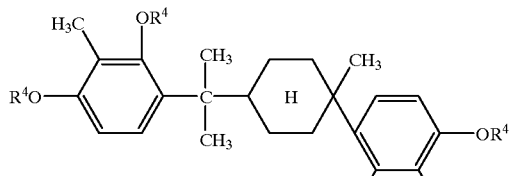

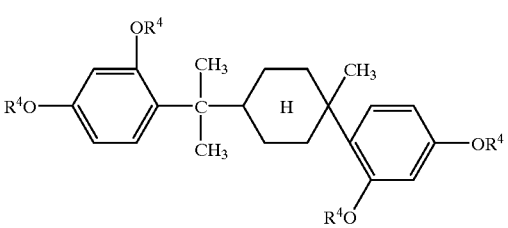

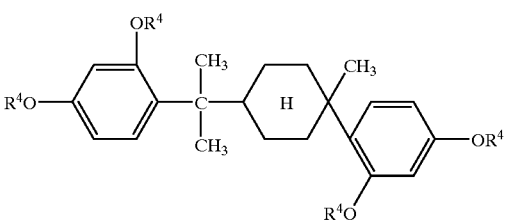

The compounds of formula (1) can be easily synthesized at low cost from phenol derivatives of the following formula (6) by a conventional method.

(6)
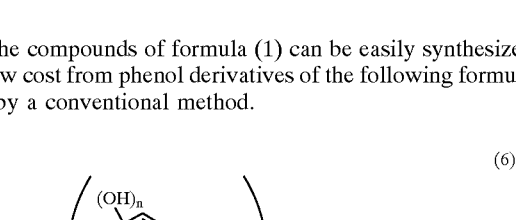

In the formula, X, $R^1$ to $R^3$, n, j, k, m, and p are as defined previously.

A compound having an acid labile group of the general formula (2a) may be synthesized by various methods. One preferred method is by reacting a phenol derivative of formula (6) with an alkene of the following formula (7):

(7)
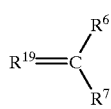

wherein $R^6$ and $R^7$ are as defined previously and $R^{19}$ is a divalent group obtained by eliminating one hydrogen atom from $R^5$, in the presence of an acid catalyst. This method can be carried out according to Japan Chemical Society Ed., "Experimental Chemistry Lecture Series, 4-th Ed., Organic Synthesis 2," Maruzene, page 200 and J. Holkombe and T. Livinghouse, J. Org. Chem., 51 (1986), pp. 111–115.

The acid catalyst used herein is not critical. Exemplary catalysts are trifluoromethanesulfonic acid, p-toluenesulfonic acid, sulfuric acid, and hydrochloric acid. The amount of the acid catalyst used is preferably 0.001 to 0.1 mol per mol of the hydroxyl group in the phenol derivative of formula (6). Reaction is preferably carried out in an organic solvent such as methylene chloride at a temperature of −40° C. to −70° C. The reaction time may be properly selected in accordance with other conditions although the reaction generally completes within about ½ to 4 hours.

A compound having an acid labile group of the general formula (2b) may be synthesized by various methods. One preferred method is by reacting a phenol derivative of formula (6) with a halogenated silylalkyl of the following formula (8):

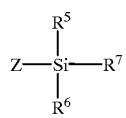

(8)

wherein Z is a halogen atom and $R^5$ to $R^7$ are as defined previously, in the presence of a base catalyst.

The base catalyst used herein is not critical. Exemplary catalysts are alkali metal salts such as sodium hydrogen carbonate, sodium carbonate, potassium hydrogen carbonate, potassium carbonate, sodium hydride, potassium hydride, sodium methylate, sodium ethylate, and potassium tert-butylate and organic bases such as triethylamine, diisopropylmethylamine, dimethylaniline, pyridine, 4-N,N-dimethylaminopyridine, and 4-(1-piperidino)pyridine. The amount of the base catalyst used is preferably 1 to 10 mol per mol of the halogenated ester of formula (8).

The reaction solvent used herein is not critical. Exemplary solvents include ethers such as tetrahydrofuran (THF), tetrahydropyran, and 1,4-dioxane; ketones such as acetone, methyl ethyl ketone, and methyl isobutyl ketone; aromatic hydrocarbons such as benzene, toluene, and xylene; halogenated hydrocarbons such as methylene chloride and chloroform; aprotic polar solvents such as N,N-dimethylformamide (DMF), N,N-dimethylacetamide, and dimethylsulfoxide, and mixtures thereof, with the tetrahydrofuran and tetrahydropyran being preferred.

A compound having an acid labile group of the general formula (2c) may be synthesized by various methods. One preferred method is by reacting a phenol derivative of formula (6) with a vinyl ether of the following formula (9):

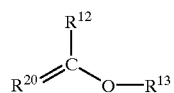

(9)

wherein $R^{12}$ and $R^{13}$ are as defined previously, or $R^{12}$ and $R^{13}$, taken together, may form a ring, and $R^{20}$ is a divalent group obtained by eliminating one hydrogen atom from $R^{11}$, in the presence of an acid catalyst.

The vinyl ether used herein is not particularly limited. Exemplary vinyl ethers include methyl vinyl ether, ethyl vinyl ether, n-propyl vinyl ether, tert-butyl vinyl ether, n-butyl vinyl ether, i-butyl vinyl ether, n-pentyl vinyl ether, and cyclohexyl vinyl ether.

The acid catalyst used herein is not critical. Exemplary catalysts are trifluoromethanesulfonic acid, p-toluenesulfonic acid, sulfuric acid, hydrochloric acid, pyridinium p-toluenesulfonate, pyridinium m-nitrobenzenesulfonate, and pyridinium sulfonate. The amount of the acid catalyst used is preferably 0.001 to 1 mol per mol of the hydroxyl group in the phenol derivative of formula (6).

The reaction solvent used herein is not critical. Exemplary solvents include ethers such as tetrahydrofuran (THF), tetrahydropyran, and 1,4-dioxane; ketones such as acetone, methyl ethyl ketone, and methyl isobutyl ketone; aromatic hydrocarbons such as benzene, toluene, and xylene; halogenated hydrocarbons such as methylene chloride and chloroform; and mixtures thereof. Preferred are tetrahydrofuran, tetrahydropyran and mixtures thereof with methylene chloride or chloroform.

Reaction is preferably carried out at a temperature of 0° C. to the boiling point of the solvent. The reaction time may be properly selected in accordance with other conditions although the reaction generally completes within about ½ to 24 hours.

At the end of reaction, the end compound of formula (1) is recovered by neutralizing the catalytic acid with an alkali, washing the solvent layer with water and concentrating it, followed by recrystallization or column fractionation.

Another preferred method for synthesizing a compound having an acid labile group of the general formula (2c) is by reacting a phenol derivative of formula (6) with a halo-alkoxyalkyl of the following formula (10):

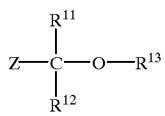

(10)

wherein Z is a halogen atom and $R^{11}$ to $R^{13}$ are as defined previously, in the presence of a base catalyst.

The halo-alkoxyalkyl used herein is not particularly limited. Examples include methoxymethyl chloride, methoxymethyl bromide, methoxymethyl iodide, ethoxymethyl chloride, ethoxymethyl bromide, and methoxyethoxymethyl chloride. The halo-alkoxyalkyl of formula (10) is preferably used in an amount of 0.1 to 10 mol per mol of the hydroxyl group in the phenol derivative of formula (6).

The base catalyst used herein is not critical. Examples include sodium hydroxide, potassium hydroxide, and sodium hydride as well as various phase transfer catalysts.

The reaction solvent used herein is not critical. Exemplary solvents include ethers such as tetrahydrofuran (THF), tetrahydropyran, and 1,4-dioxane; ketones such as acetone, methyl ethyl ketone, and methyl isobutyl ketone; aromatic hydrocarbons such as benzene, toluene, and xylene; halogenated hydrocarbons such as methylene chloride and chloroform; and mixtures thereof. A two-layer system of an organic solvent and water is useful in the case of phase transfer reaction. Preferred are tetrahydrofuran, tetrahydropyran and a two-layer system of methylene chloride and water.

Reaction is preferably carried out at a temperature of 0° C. to the boiling point of the solvent. The reaction time may be properly selected in accordance with other conditions although the reaction generally completes within about ½ to 24 hours.

A compound having an acid labile group of the general formula (2d) wherein q=0 may be synthesized by various methods. Easiest and most preferred method is by reacting a phenol derivative of formula (6) with a dicarbonic acid diester of the following formula (11):

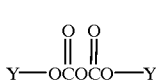 (11)

wherein Y is as defined previously, in the presence of a base catalyst. The dicarbonic acid diester of formula (11) is preferably used in an amount of 0.1 to 10 mol per mol of the hydroxyl group in the phenol derivative of formula (6).

The base catalyst used herein is not critical. Exemplary catalysts are alkali metal salts such as sodium hydrogen carbonate, sodium carbonate, potassium hydrogen carbonate, potassium carbonate, sodium hydride, potassium hydride, sodium methylate, sodium ethylate, and potassium tert-butylate and organic bases such as triethylamine, diisopropylmethylamine, dimethylaniline, pyridine, 4-N,N-dimethylaminopyridine, and 4-(1-piperidino)pyridine. The amount of the base catalyst used is preferably 1 to 10 mol per mol of the dicarbonic acid diester of formula (11).

The reaction solvent used herein is not critical. Exemplary solvents include ethers such as tetrahydrofuran (THF), tetrahydropyran, and 1,4-dioxane; ketones such as acetone, methyl ethyl ketone, and methyl isobutyl ketone; aromatic hydrocarbons such as benzene, toluene, and xylene; halogenated hydrocarbons such as methylene chloride and chloroform; aprotic polar solvents such as N,N-dimethylformamide (DMF), N,N-dimethylacetamide, and dimethylsulfoxide, and mixtures thereof, with the tetrahydrofuran and tetrahydropyran being preferred.

Reaction is preferably carried out at a temperature of 0° C. to the boiling point of the solvent. The reaction time may be properly selected in accordance with other conditions although the reaction generally completes within about ½ to 24 hours.

A compound having an acid labile group of the general formula (2d) wherein q=1 and $R^{14}$ is a divalent aliphatic (chain or cyclic) or divalent aromatic substituent may be synthesized by various methods. Easiest and most preferred method is by reacting a phenol derivative of formula (6) with a halogenated ester of the following formula (12):

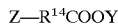 (12)

wherein Z is a halogen atom, $R^{14}$ and Y are as defined previously, in the presence of a base catalyst.

The halogenated ester of formula (12) is not particularly limited. Examples include tert-butyl chloroacetate, tert-butyl bromoacetate, 1,1-dimethylpropyl chloroacetate, 1,1-dimethylbutyl chloroacetate, trimethylsilyl chloroacetate, methoxymethyl chloroacetate, ethoxymethyl chloroacetate, ethoxymethoxymethyl chloroacetate, ethoxyethyl chloroacetate, n-butoxyethyl chloroacetate, tetrahydrofuranyl chloroacetate, tetrahydropyranyl chloroacetate, tert-butyl chloropropionate, tert-butyl chlorobutyrate, and tert-butyl chlorovalerate.

The halogenated ester of formula (12) is preferably used in an amount of 0.1 to 10 mol per mol of the hydroxyl group in the phenol derivative of formula (6).

The base catalyst used herein is not critical. Exemplary catalysts are alkali metal salts such as sodium hydrogen carbonate, sodium carbonate, potassium hydrogen carbonate, potassium carbonate, sodium hydride, potassium hydride, sodium methylate, sodium ethylate, and potassium tert-butylate and organic bases such as triethylamine, diisopropylmethylamine, dimethylaniline, pyridine, 4-N,N-dimethylaminopyridine, and 4-(1-piperidino)pyridine. The amount of the base catalyst used is preferably 1 to 10 mol per mol of the halogenated ester of formula (12).

The reaction solvent used herein is not critical. Exemplary solvents include alcohols such as methanol, ethanol, propanol, 2-methylethanol, butanol, and tert-butyl alcohol; ketones such as acetone, methyl ethyl ketone, and methyl isobutyl ketone; aromatic hydrocarbons such as benzene, toluene, and xylene; halogenated hydrocarbons such as methylene chloride and chloroform; aprotic polar solvents such as N,N-dimethylformamide (DMF), N,N-dimethylacetamide, and dimethylsulfoxide, and mixtures thereof, with the acetone, N,N-dimethylformamide, and N,N-dimethylacetamide being preferred.

Reaction is preferably carried out at a temperature of 0° C. to the boiling point of the solvent. The reaction time may be properly selected in accordance with other conditions although the reaction generally completes within about ½ to 24 hours.

The compound of formula (1) is useful as a dissolution rate regulator of a chemically amplified positive resist composition. In this regard, the dissolution rate regulator according to the invention is defined as comprising a compound of formula (1) or a mixture of two or more compounds of formula (1). In either case, the percent replacement of the hydrogen atom of a phenolic hydroxyl group by an acid labile group, that is, the content of an acid labile group in the entire $R^4$ groups should preferably be 10 to 100 mol %, more preferably 30 to 100 mol %, most preferably 50 to 100 mol %. A content of an acid labile group in the entire $R^4$ groups in the range of 10 to 100 mol % is used herein to encompass both a compound of formula (1) wherein the content of an acid labile group in the entire $R^4$ groups in its molecule is in the range of 10 to 100 mol % and a mixture in which at least one compound of formula (1) wherein the entire $R^4$ groups are hydrogen atoms is mixed with at least one compound of formula (1) wherein at least one $R^4$ group is an acid labile group such that 10 to 100 mol % of the entire $R^4$ groups in the mixture is an acid labile group.

In the further aspect, the present invention provides a chemically amplified positive resist composition of the three component system essentially comprising the above-mentioned dissolution rate regulator. More specifically, the chemically amplified positive resist composition is defined as comprising (A) an organic solvent, (B) an alkali soluble resin, (C) a photoacid generator, and (D) a dissolution rate regulator comprising a compound of formula (1), and optionally, (E) another dissolution rate regulator.

Examples of the organic solvent (A) include ketones such as cyclohexanone, 2-heptanone, 3-heptanone, 4-heptanone, and methyl-2-n-amylketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, diethylene glycol dimethyl ether, ethylene glycol-tert-butyl ether methyl ether (1-tert-butoxy-2-methoxyethane), and ethylene glycol-tert-butyl ether ethyl ether (1-tert-butoxy-2-ethoxyethane); and esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and methyl β-methoxyisobutyrate alone or in admixture of two or more. The preferred solvents are 1-ethoxy-2-propanol ensuring solubility of resist components and propylene glycol monomethyl ether acetate (α and β types) ensuring safety and solubility of resist components.

The alkali soluble resin (B) as the base resin includes polyhydroxystyrene and derivatives thereof. Preferred are those polyhydroxystyrene derivatives wherein the hydrogen atom of some OH groups is replaced by at least one acid labile group and hydroxystyrene copolymers. In the former, examples of the acid labile group used therein include substituents of tert-butyl derivatives such as tert-butyl, tert-butoxycarbonyl, and tert-butoxycarbonylmethyl groups; normal or branched chain acetal groups such as 1-ethoxyethyl, 1-n-propoxyethyl, 1-isopropoxyethyl, 1-n-butoxyethyl, 1-isobutoxyethyl, 1-sec-butoxyethyl, 1-tert-butoxyethyl, 1-tert-pentoxyethyl, 1-ethoxy-n-propyl, and 1-cyclohexylethyl groups; and cyclic acetal groups such as tetrahydrofuranyl, tetrahydropyranyl, and 2-methoxytetrahydropyranyl groups. These acid labile groups may be present alone or in admixture of two or more on a common polymer chain. Preferred combinations of two substituents on a common polymer chain are combinations of tert-butoxycarbonyl with 1-ethoxyethyl, tert-butoxycarbonyl with 1-n-butoxyethyl, and tert-butoxycarbonyl with 1-ethoxy-n-propyl. The polyhydroxystyrene derivatives should preferably have a weight-average molecular weight of about 3,000 to about 100,000.

Included in the hydroxystyrene copolymers are copolymers of hydroxystyrene and styrene, copolymers of hydroxystyrene and tert-butyl acrylate, copolymers of hydroxystyrene and tert-butyl methacrylate, copolymers of hydroxystyrene and maleic anhydride, and copolymers of hydroxystyrene and di-tert-butyl maleate.

The polyhydroxystyrene or derivatives thereof should preferably have a weight-average molecular weight (Mw) of about 3,000 to about 100,000. Film formability and resolution would be poor with Mw of less than 3,000 whereas resolution would be poor with Mw of more than 100,000.

Any of well-known photo-acid generators may be used as component (C). One preferred class of photo-acid generators consists of onium salts of the following general formula (13):

$$(R)_r MA \qquad (13)$$

wherein R groups, which may be identical or different, are selected from substituted or unsubstituted aromatic groups and alkyl groups, M is sulfonium or iodonium, A is p-toluenesulfonate, trifluoromethanesulfonate, nonafluorobutanesulfonate, butanesulfonate or normal, branched or cyclic alkylsulfonate having 1 to 20 carbon atoms, and letter r is 2 or 3. Examples of the aromatic group represented by R include phenyl, tert-butoxyphenyl, tert-butylphenyl, tert-butoxycarbonyloxyphenyl, tert-butoxycarbonylmethoxyphenyl, tert-butyldimethylsilyloxyphenyl, tetrahydrofuranyloxyphenyl, 1-ethoxyethoxyphenyl, 1-propoxyethoxyphenyl, and 1-tert-butoxyethoxyphenyl groups. The alkyl groups represented by R may be normal, branched or cyclic and include methyl, ethyl, cyclohexyl, and 2-oxocyclohexyl groups.

Other useful examples of the photo-acid generator are

β-ketosulfone derivatives such as 2-cyclohexylcarbonyl-2-(p-toluenesulfonyl)propane and 2-isopropylcarbonyl-2-(p-toluenesulfonyl)propane;

pyrogallolsulfonic acid ester derivatives such as 1,2,3-tris(methanesulfonyloxy)benzene, 1,2,3-tris(trifluoromethanesulfonyloxy)benzene, 1,2,3-tris(n-butanesulfonyloxy)benzene, 1,2,3-tris(p-toluenesulfonyloxy)benzene, and 1,2,3-tris((+)10-camphorsulfonyloxy)benzene;

nitrobenzylsulfonic acid derivatives such as 2-nitrobenzyltosylate, 2,6-dinitrobenzyltosylate, and 2,4-dinitrobenzyltosylate;

diazonaphthoquinone sulfonic acid ester derivatives such as 3,4,5-tris(5-diazonaphthoquinonesulfonyloxy) benzophenone and 3,4,5-tris(4-diazonaphthoquinonesulfonyloxy)benzophenone;

α,α'-bisaryl or bisalkylsulfonyldiazomethane derivatives such as α,α'-bisphenylsulfonyldiazomethane, α,α'-bis (p-tert-butylphenylsulfonyl)diazomethane, α,α'-bis(p-tert-butoxyphenylsulfonyl)diazomethane, α,α'-bis(tert-butylsulfonyl)diazomethane, and α,α'-biscyclohexylsulfonyldiazomethane;

N-sulfonyloxyimide derivatives such as N-trifluoromethanesulfonyloxyphthalimide, N-(p-toluenesulfonyloxy)phthalimide, N-trifluoromethanesulfonyloxysuccinimide, N-(p-toluenesulfonyloxy)succinimide, N-camphorsulfonyloxynaphthalimide, 5-norbornene-2,3-dicarboxyimide-yl-triflate, 5-norbornene-2,3-dicarboxyimide-yl-tosylate, and 5-norbornene-2,3-dicarboxyimide-yl-n-butylsulfonate; and disulfone derivatives such as diphenyl disulfone and dicyclohexyl disulfone.

Exemplary compounds suitable as a photo-acid generator are shown below. They may be used alone or in admixture of two or more.

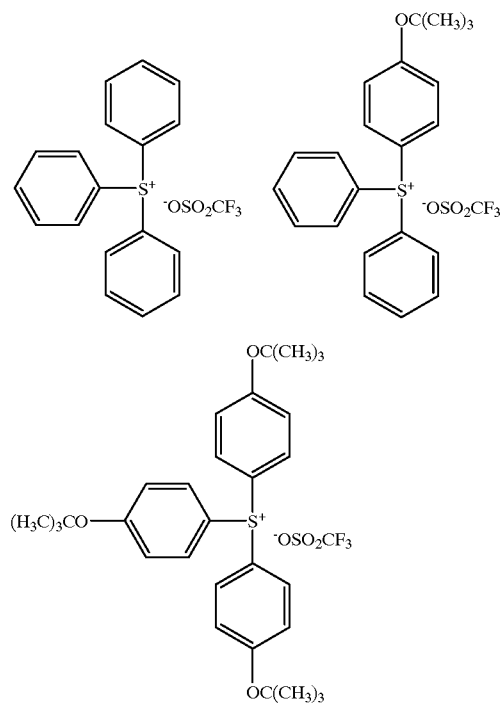

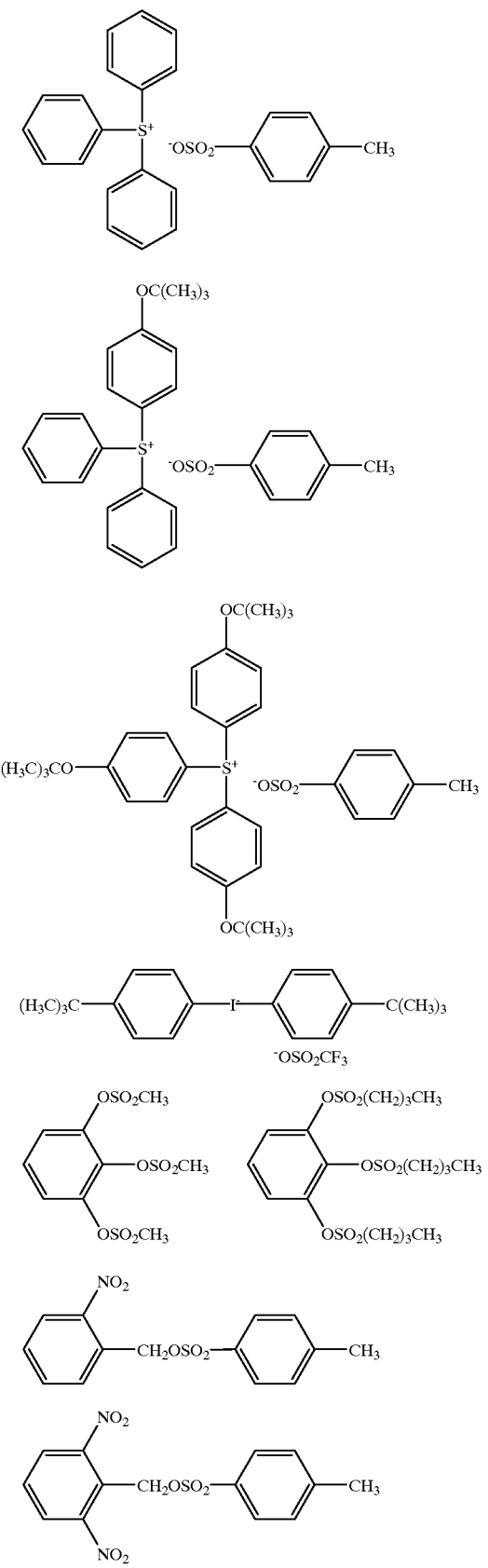

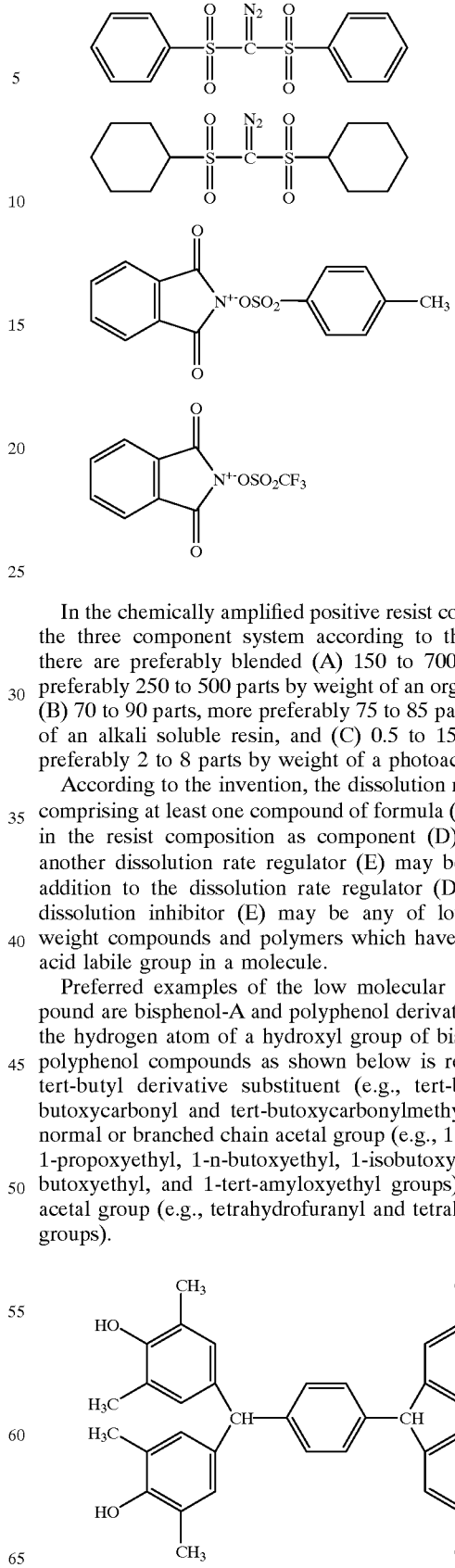

In the chemically amplified positive resist composition of the three component system according to the invention, there are preferably blended (A) 150 to 700 parts, more preferably 250 to 500 parts by weight of an organic solvent, (B) 70 to 90 parts, more preferably 75 to 85 parts by weight of an alkali soluble resin, and (C) 0.5 to 15 parts, more preferably 2 to 8 parts by weight of a photoacid generator.

According to the invention, the dissolution rate regulator comprising at least one compound of formula (1) is blended in the resist composition as component (D). If desired, another dissolution rate regulator (E) may be blended in addition to the dissolution rate regulator (D). The other dissolution inhibitor (E) may be any of low molecular weight compounds and polymers which have at least one acid labile group in a molecule.

Preferred examples of the low molecular weight compound are bisphenol-A and polyphenol derivatives wherein the hydrogen atom of a hydroxyl group of bisphenol-A or polyphenol compounds as shown below is replaced by a tert-butyl derivative substituent (e.g., tert-butoxy, tert-butoxycarbonyl and tert-butoxycarbonylmethyl groups), a normal or branched chain acetal group (e.g., 1-ethoxyethyl, 1-propoxyethyl, 1-n-butoxyethyl, 1-isobutoxyethyl, 1-tert-butoxyethyl, and 1-tert-amyloxyethyl groups) or a cyclic acetal group (e.g., tetrahydrofuranyl and tetrahydropyranyl groups).

-continued

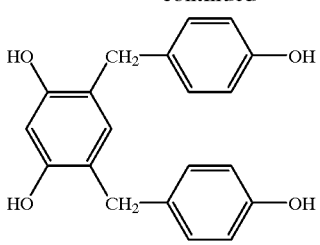

Examples of the polymeric dissolution inhibitor include copolymers of p-butoxystyrene and tert-butyl acrylate and copolymers of p-butoxystyrene and maleic anhydride. These copolymers should preferably have a weight-average molecular weight of 500 to 10,000.

The amount of the dissolution rate regulator (D) or compound of formula (1) blended is preferably 1 to 40 parts, especially 5 to 25 parts. Less than 1 part of dissolution rate regulator (D) would be ineffective for inhibiting dissolution whereas more than 40 parts would adversely affect the heat resistance of resist film. The amount of the other dissolution rate regulator (E), if blended, is preferably 1 to 40 parts, especially 5 to 25 parts.

The resist composition of the invention may further contain various additives, for example, a carboxylic acid derivative and nitrogenous compound for improving PED stability, a surface-active agent for facilitating coating, and a light-absorbing agent for reducing irregular reflection from the substrate.

Examples of the carboxylic acid derivative include 4-hydroxyphenylacetic acid, 3-hydroxyphenylacetic acid, 2-hydroxyphenylacetic acid, 3-(4-hydroxyphenyl)propionic acid, 3-(2-hydroxyphenyl)propionic acid, 2,5-dihydroxyphenylacetic acid, 3,4-dihydroxyphenylacetic acid, 1,2-phenylenediacetic acid, 1,3-phenylenediacetic acid, 1,4-phenylenediacetic acid, 1,2-phenylenedioxydiacetic acid, 1,4-phenylenedipropanoic acid, benzoic acid, 4,4-(4-hydroxyphenyl)valeric acid, 4-tert-butoxyphenylacetic acid, 4-(4-hydroxyphenyl)butyric acid, 3,4-dihydroxymandelic acid, and 4-hydroxymandelic acid. The amount of the carboxylic acid derivative blended in the resist composition of the invention is preferably 0.1 to 15 parts, especially 1 to 10 parts by weight.

Included in the nitrogenous compound are primary, secondary and tertiary aliphatic amines, hybrid amines, aromatic amines, heterocyclic amines, carboxyl-bearing nitrogenous compounds, sulfonyl-bearing nitrogenous compounds, hydroxyl-bearing nitrogenous compounds, hydroxyphenyl-bearing nitrogenous compounds, alcoholic nitrogenous compounds, and amide derivatives.

Examples of the primary aliphatic amine include ammonia, methylamine, ethylamine, propylamine, butylamine, pentylamine, amylamine, hexylamine, heptylamine, octylamine, nonylamine, decylamine, laurylamine, cetylamine, methylenediamine, ethylenediamine, and tetraethylenediamine. Examples of the secondary aliphatic amine include dimethylamine, diethylamine, dipropylamine, dibutylamine, dipentylamine, dihexylamine, diheptylamine, dioctylamine, dinonylamine, didecylamine, dimethylmethylenediamine, dimethylethylenediamine, and dimethyltetraethylenediamine. Examples of the tertiary aliphatic amine include trimethylamine, triethylamine, tripropylamine, tributylamine, tripentylamine, trihexylamine, triheptylamine, trioctylamine, tetramethylmethylenediamine, tetramethylethylenediamine, and tetramethyltetraethylenediamine.

Examples of the hybrid amine include dimethylethylamine and methylethylpropylamine. Examples of the aromatic and heterocyclic amines include benzylamine, phenethylamine, benzyldimethylamine, aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 4-nitroaniline, and dinitroaniline), toluidine derivatives (e.g., toluidine and N,N-dimethyltoluidine), quinoline, aminobenzoic acid, N-phenylphenyltolylamine, N-methyldiphenylamine, triphenylamine, phenylenediamine, naphthylamine, diaminonaphthalene, pyrrole derivatives (e.g., pyrrole, methylpyrrole, dimethylpyrrole, and N-methylpyrrole), imidazole derivatives (e.g., imidazole, 4-methylimidazole, and 4-methyl-2-phenylimidazole), oxazole derivatives, thiazole derivatives, pyrazole derivatives, pyrrolidine derivatives (e.g., pyrrolidine, N-methylpyrrolidone and N-methylpyrrolidine), pyrroline derivatives, pyridine derivatives (e.g., pyridine, methylpyridine, ethylpyridine, propylpyridine, butylpyridine, 5-butyl-2-methylpyridine, trimethylpyridine, triethylpyridine, phenylpyridine, 3-methyl-2-phenylpyridine, tert-butylpyridine, diphenylpyridine, benzylpyridine, methoxypyridine, butoxypyridine, dimethoxypyridine, 1-methyl-2-pyridone, 4-pyrrolidinylpyridine, 1-methyl-4-phenylpyridine, 2-(1-ethylpropyl)pyridine, etc.), piperidine derivatives, pyrimidine derivatives, purine derivatives, quinoline derivatives, carbazole derivatives, indole derivatives, nicotinic amide derivatives, adenosine derivatives, adenine derivatives, thiabenzole, and diaminosulfone.

Examples of the carboxyl-bearing nitrogenous compound include amino acid derivatives such as nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine. Examples of the sulfonyl-bearing nitrogenous compound, hydroxyl-bearing nitrogenous compound, hydroxyphenyl-bearing nitrogenous compound, and alcoholic nitrogenous compound include 2-hydroxypyridine, aminocresole, thiaminenaphthalene disulfonic salts, pyridinesulfonic acid, ethanolamine, diethanolamine, triethanolamine, diisopropylamine, triisopropylamine, tripropylamine, 1-aminobutane-2-diol, 1-aminopropan-3-ol, and 1-aminobutane-2-diol. Examples of the amide derivative include formamide, N-methylformamide, N,N-dimethylformamide, acetamide, N-methylacetamide, N,N-dimethylacetamide, propionamide, and benzamide.

Preferably the nitrogenous compound is blended in an amount of 0.001 to 10 parts, especially 0.01 to 1 part by weight per part by weight of the photoacid generator. Less than 0.001 part would be ineffective whereas more than 10 parts of the nitrogenous compound would adversely affect resolution and sensitivity.

Examples of the surfactant include perfluoroalkylpolyoxyethylene ethanols, fluorinated alkyl esters, perfluoroalkylamine oxides, and perfluoroalkyl EO addition products.

Examples of the light-absorbing agent include diaryl sulfoxides, diaryl sulfones, 9,10-dimethylanthracene, and 9-fluorenone.

Any well-known lithography may be used to form a resist pattern from a positive resist composition of the invention. The resist composition of the invention is especially suitable for fine patterning with deep-UV radiation of 254 to 193 nm and electron beams.

When used as a dissolution rate regulator, the compound of formula (1) exerts remarkably enhanced dissolution inhibitory effect and minimized light absorption in the deep-ultraviolet region. A chemically amplified positive resist composition having the compound of formula (1) blended therein is highly sensitive to actinic radiation such as deep-UV radiation, electron beam and X-ray, especially KrF excimer laser light, and has improved sensitivity, resolution and plasma etching resistance. The resulting resist pattern is fully resistant to heat. The resist composition has high resolution enough to lend itself to fine patterning.

EXAMPLE

Examples of the present invention are given below by way of illustration and not by way of limitation. All parts are by weight.

Synthesis Example 1

Synthesis of 2-(4-tert-butoxycarbonyloxyphenyl)-2-{4-(4-tert-butoxycarbonyloxyphenyl-4-methyl)cyclohexyl}propane corresponding to formula (5f) wherein $R^4$=tert-butoxycarbonyl In a mixture of 30 grams of THF and 14 grams of pyridine was dissolved 12.9 grams (0.04 mol) of 2-(4-hydroxyphenyl)-2-{4-(4-methyl-4-hydroxyphenyl)cyclohexyl}-propane corresponding to formula (5f) wherein $R^4$ is H. With stirring at room temperature, a mixture of 21.0 grams (0.096 mol) of di-tert-butyl dicarbonate and 8 grams of THF was added to the solution. The solution was stirred for 4 hours at a temperature of 15 to 30° C. At the end of reaction, the solvent was distilled off in vacuum, yielding white brown crystals. The crystals were purified by silica gel chromatography (eluent: ethyl acetate/hexane), obtaining 2-(4-tert-butoxycarbonyloxyphenyl)-2-{4-(4-tert-butoxycarbonyloxyphenyl-4-methyl)cyclohexyl}propane corresponding to formula (5f) wherein $R^4$ is a tert-butoxycarbonyl group, that is, the structural formula shown below. Amount 12.0 grams, yield 57.1%, purity 99.0%.

The product, 2-(4-tert-butoxycarbonyloxyphenyl)-2-{4-(4-tert-butoxycarbonyloxyphenyl-4-methyl)cyclohexyl}-propane was examined by nuclear magnetic resonance (NMR) spectroscopy, infrared (IR) absorption spectroscopy, and elemental analysis. The results are shown below.

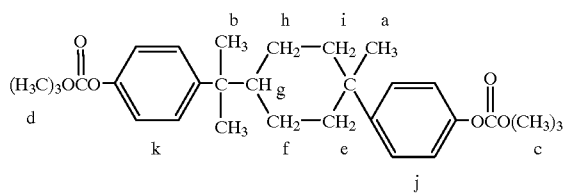

$^1$H-NMR: CDCl$_3$, δ (ppm)

| (a) | 0.72–0.82 | quadruplet | 3H |
|---|---|---|---|
| (b) | 1.23–1.31 | doublet | 6H |
| (c,d) | 1.53–1.54 | doublet | 18H |
| (e,f,g,h,i) | 0.61–2.77 | multiplet | 9H |
| (j,k) | 7.12–7.35 | multiplet | 8H |

IR: (cm$^{-1}$)

3039, 2977, 2935, 2871, 1893, 1756, 1660, 1604, 1508, 1473, 1457, 1394, 1274, 1220, 1147, 1049, 1014, 896, 869, 836, 819, 782, 754, 713, 698, 603, 568, 553, 545, 462

-continued

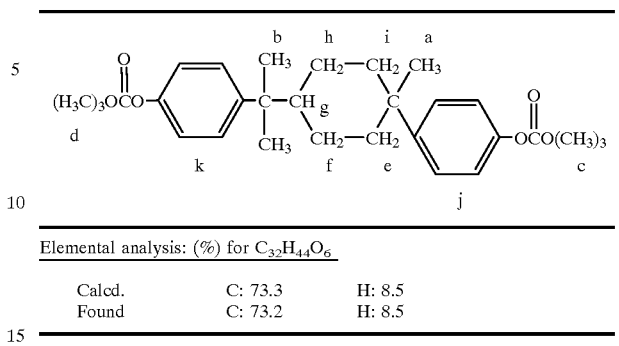

Elemental analysis: (%) for $C_{32}H_{44}O_6$

| Calcd. | C: 73.3 | H: 8.5 |
|---|---|---|
| Found | C: 73.2 | H: 8.5 |

Synthesis Example 2

Synthesis of 2-{4-(1-ethoxyethoxy)phenyl}-2-[4-{4-(1-ethoxyethoxy)phenyl-4-methyl}cyclohexyl]propane corresponding to formula (5f) wherein $R^4$=ethoxyethyl In a mixture of 66 grams of THF and 55 grams of dichloromethane was dissolved 12.9 grams (0.04 mol) of 2-(4-hydroxyphenyl)-2-{4-(4-methyl-4-hydroxyphenyl)cyclohexyl}propane corresponding to formula (5f) wherein $R^4$ is H. With stirring at room temperature, 17.3 grams (0.24 mol) of ethyl vinyl ether was added dropwise to the solution. After the solution was stirred for 20 minutes, 1.0 gram (0.004 mol) of pyridinium p-toluenesulfonate was added and dissolved therein. The solution was stirred at room temperature for 8 hours. The reaction solution was ice cooled, 78 grams of a 0.6% aqueous solution of sodium hydrogen carbonate was added to neutralize the acid to terminate reaction. From an organic layer separated from the reaction solution, the solvent was distilled off in vacuum, yielding oily matter. The oil was purified by silica gel chromatography (eluent: ethyl acetate/hexane), obtaining 2-{4-(1-ethoxyethoxy)phenyl}-2-[4-{4-(1-ethoxyethoxy)phenyl-4-methyl}cyclohexyl]propane of the structural formula shown below. Amount 12.0 grams, yield 64.2%, purity 97.0%.

The product, 2-{4-(1-ethoxyethoxy)phenyl}-2-[4-{4-(1-ethoxyethoxy)phenyl-4-methyl}cyclohexyl]propane was examined by NMR spectroscopy, IR spectroscopy, and elemental analysis. The results are shown below.

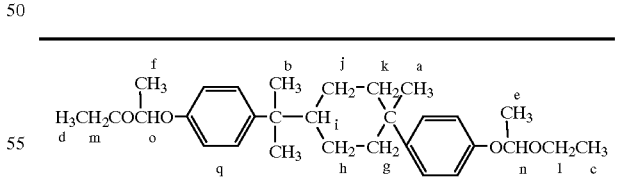

$^1$H-NMR: CDCl$_3$, δ (ppm)

| (a) | 0.74–0.84 | quadruplet | 3H |
|---|---|---|---|
| (b) | 1.20–1.21 | doublet | 6H |
| (c,d) | 1.23–1.32 | doublet | 6H |
| (e,f) | 1.46–1.49 | quadruplet | 6H |
| (g,h,i,j,k) | 0.60–2.78 | multiplet | 9H |
| (l,m) | 3.49–3.81 | multiplet | 4H |
| (n,o) | 5.32–5.34 | multiplet | 2H |
| (p,q) | 6.87–7.29 | multiplet | 8H |

-continued

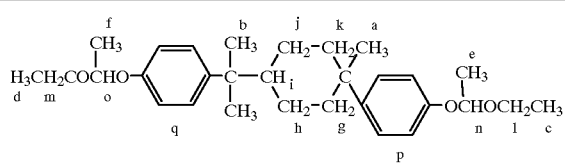

IR: (cm$^{-1}$)

3095, 2973, 2931, 2871, 1886, 1608, 1579, 1510, 1444,
1440, 1382, 1344, 1290, 1240, 1182, 1120, 1078, 1049,
1014, 945, 902, 831, 730, 638, 559

Elemental analysis: (%) for $C_{30}H_{44}O_4$

| | | |
|---|---|---|
| Calcd. | C: 76.9 | H: 9.5 |
| Found | C: 76.9 | H: 9.5 |

Synthesis Example 3

Synthesis Example 1 was repeated except that n-propyl vinyl ether was used instead of the ethyl vinyl ether used in Synthesis Example 1, yielding 2-{4-(1-n-propoxyethoxy)phenyl}-2-[4-{4-(1-n-propoxyethoxy)phenyl-4-methyl}cyclohexyl]propane corresponding to formula (5f) wherein $R^4$ is a n-propoxyethyl group. Purity 97.5%, yield 60.3%.

Synthesis Example 4

Synthesis Example 1 was repeated except that tert-butyl vinyl ether was used instead of the ethyl vinyl ether used in Synthesis Example 1, yielding 2-{4-(1-tert-butoxyethoxy)phenyl}-2-[4-{4-(1-tert-butoxyethoxy)phenyl-4-methyl}cyclohexyl]propane corresponding to formula (5f) wherein $R^4$ is a tert-butoxyethyl group. Purity 98.0%, yield 54.6%.

Synthesis Example 5

Synthesis Example 1 was repeated except that n-butyl vinyl ether was used instead of the ethyl vinyl ether used in Synthesis Example 1, yielding 2-{4-(1-n-butoxyethoxy)phenyl}-2-[4-{4-(1-n-butoxyethoxy)phenyl-4-methyl}cyclohexyl]propane corresponding to formula (5f) wherein $R^4$ is a n-butoxyethyl group. Purity 97.8%, yield 55.8%.

Synthesis Example 6

Synthesis Example 1 was repeated except that i-butyl vinyl ether was used instead of the ethyl vinyl ether used in Synthesis Example 1, yielding 2-{4-(1-1-butoxyethoxy)phenyl}-2-{4-{4-(1-1-butoxyethoxy)phenyl-4-methyl}cyclohexyl}propane corresponding to formula (5f) wherein $R^4$ is an i-butoxyethyl group. Purity 97.8%, yield 50.7%.

Synthesis Example 7

Synthesis of 2-(4-dimethoxymethoxyphenyl)-2-{4-(4-dimethoxymethoxyphenyl-4-methyl)cyclohexyl}propane A four-necked flask equipped with a Dimroth condenser lo was charged with 42.2 grams (0.13 mol) of 2-(4-hydroxyphenyl)-2-{4-(4-methyl-4-hydroxyphenyl)cyclohexyl}propane corresponding to formula (5f) wherein $R^4$ is H and 582 grams (5.4 mol) of methyl o-formate, to which 0.6 gram of p-toluenesulfonic acid was added. The flask was heated at 130° C. to continue reaction for 3 hours while methanol by-product was distilled off through the Dimroth condenser. The reaction solution was cooled to room temperature, combined with 410 grams of a 0.5% aqueous solution of potassium carbonate, and stirred. After 300 grams of diethyl ether was added to the reaction solution, an organic layer was extracted. The solvent was distilled off. By purification through a silica gel chromatograph (eluent: chloroform), 2-(4-dimethoxymethoxyphenyl)-2-{4-(4-dimethoxymethoxyphenyl-4-methyl)cyclohexyl}propane corresponding to formula (5f) wherein $R^4$ is a dimethoxymethyl group was isolated as a colorless clear liquid. Amount 52.8 grams, yield 85.9%, purity 98.9%.

Synthesis Example 8

Synthesis Example 7 was repeated except that ethyl o-formate was used instead of the methyl o-formate used in Synthesis Example 7, yielding 2-(4-diethoxymethoxyphenyl)-2-{4-(4-diethoxymethoxyphenyl-4-methyl)cyclohexyl}propane corresponding to formula (5f) wherein $R^4$ is a diethoxymethyl group. Purity 98.1%, yield 89.6%.

Synthesis Example 9

Synthesis of 2-(4-tert-butoxyphenyl)-2-{4-(4-methyl-4-tert-butoxyphenyl)cyclohexyl}propane corresponding to formula (5f) wherein $R^4$=tert-butyl In a mixture of 24 grams of THF and 43 grams of methylene chloride was dissolved 16.2 grams (0.05 mol) of 2-(4-hydroxyphenyl)-2-{4-(4-methyl-4-hydroxyphenyl)cyclohexyl}propane corresponding to formula (5f) wherein $R^4$ is H. The solution was cooled to −30° C. with a dry ice/methanol bath. With stirring, 79.2 grams (1.4 mol) of liquid isobutene was added and 1.8 grams (0.012 mol) of trifluoromethanesulfonic acid was then added. Stirring was continued for 3 hours while keeping the reaction solution at a temperature of −10° C. to −5° C. Reaction was stopped by adding 2.4 grams (0.024 mol) of triethylamine to the reaction solution for neutralizing the acid. The reaction solution was mixed with 100 grams of chloroform and then washed three times with 100 grams of water. The solvent was distilled off from the organic layer, obtaining oily matter. The oil was purified by silica gel chromatography (eluent: chloroform/methanol), isolating 2-(4-tert-butoxyphenyl)2-{4-(4-methyl-4-tert-butoxyphenyl)cyclohexyl}propane corresponding to formula (5f) wherein $R^4$ is a tert-butyl group. Amount 13.1 grams, yield 60.1%, purity 98.9%.

Synthesis Example 10

Synthesis of 2-(4-tert-butoxycarbonylmethyloxyphenyl)-2-{4-(4-methyl-4-tert-butoxycarbonylmethyloxyphenyl)cyclohexyl}propane corresponding to formula (5f) wherein $R^4$=tert-butoxycarbonylmethyl In 70 grams of DMF were dissolved 12.9 grams (0.04 mol) of 2-(4-hydroxyphenyl)-2-{4-(4-methyl-4-hydroxyphenyl)cyclohexyl}propane corresponding to formula (5f) wherein $R^4$ is H and 13.3 grams of tert-butyl chloroacetate. With 12.2 grams of potassium carbonate added, reaction was carried out for 7 hours at 100° C. At the end of reaction, the precipitated inorganic salt was removed by filtration and the solvent was distilled off, obtaining crude crystals. By purification through a silica gel chromatograph (eluent: ethyl acetate/hexane), 2-(4-tert-butoxycarbonylmethyloxyphenyl)-2-{4-(4-methyl-4-tert-butoxycarbonylmethyloxyphenyl)cyclohexyl}propane was isolated. Amount 13.4 grams, yield 60.8%, purity 99.1%.

Synthesis Example 11

Synthesis of a compound of formula (1) wherein 33% of $R^4$ is tert-butoxycarbonyl and 67% of $R^4$ is hydrogen Synthesis Example 1 was repeated except that the amount of di-tert-butyl dicarbonate was changed to 5.8 grams (0.026 mol), yielding a compound of formula (5f) wherein 33% of $R^4$ is tert-butoxycarbonyl group and 67% of $R^4$ is hydrogen atom. The percent replacement was confirmed by NMR analysis. Yield 55.0%.

Synthesis Example 12

Synthesis of a compound of formula (1) wherein 50% of $R^4$ is tert-butoxycarbonyl and 50% of $R^4$ is hydrogen Synthesis Example 1 was repeated except that the amount of di-tert-butyl dicarbonate was changed to 8.7 grams (0.040 mol), yielding a compound of formula (5f) wherein 50% of $R^4$ is tert-butoxycarbonyl group and 50% of $R^4$ is hydrogen atom. The percent replacement was confirmed by NMR analysis. Yield 52.5%.

Synthesis Example 13

Synthesis of a compound of formula (1) wherein 35% of $R^4$ is ethoxyethyl and 65% of $R^4$ is hydrogen Synthesis Example 2 was repeated except that the amount of ethyl vinyl ether was changed to 6.3 grams (0.088 mol), yielding a compound of formula (5f) wherein 35% of $R^4$ is ethoxyethyl group and 65% of $R^4$ is hydrogen atom. The percent replacement was confirmed by NMR analysis. Yield 59.9%.

Synthesis Example 14

Synthesis of a compound of formula (1) wherein 50% of $R^4$ is ethoxyethyl and 50% of $R^4$ is hydrogen Synthesis Example 2 was repeated except that the amount of ethyl vinyl ether was changed to 9.5 grams (0.13 mol), yielding a compound of formula (5f) wherein 50% of $R^4$ is ethoxyethyl group and 50% of $R^4$ is hydrogen atom. The percent replacement was confirmed by NMR analysis. Yield 58.0%.

Synthesis Examples 15–28

Reaction was carried out as in Synthesis Examples 1 to 10 except that 2-(3,4-dihydroxyphenyl)-2-{4-(4-methyl-3,4-dihydroxyphenyl)cyclohexyl}propane corresponding to formula (5m) wherein $R^4$=H was used instead of the 2-(4-hydroxyphenyl)-2-{4-(4-methyl-4-hydroxyphenyl)cyclohexyl}propane corresponding to formula (5f) wherein $R^4$=H used in Synthesis Examples 1 to 10, obtaining the following compounds, respectively.

Synthesis Example 15

2-(3,4-di-tert-butoxycarbonyloxyphenyl)-2-{4-(4-methyl-3,4-di-tert-butoxycarbonyloxyphenyl)cyclohexyl}propane corresponding to formula (5m) wherein $R^4$=tert-butoxycarbonyl Purity 99.1%, yield 45.9%

Synthesis Example 16

2-{3,4-di(1-ethoxyethoxy)phenyl}-2-[4-{4-methyl-3,4-di(1-ethoxyethoxy)phenyl}cyclohexyl]propane corresponding to formula (5m) wherein $R^4$=ethoxyethyl Purity 98.5%, yield 50.1%

Synthesis Example 17

2-{3,4-di(1-n-propoxyethoxy)phenyl}-2-[4-{4-methyl-3,4-di(1-n-propoxyethoxy)phenyl}cyclohexyl]propane corresponding to formula (5m) wherein $R^4$=1-n-propoxyethyl Purity 98.5%, yield 57.8%

Synthesis Example 18

2-{3,4-di(1-tert-butoxyethoxy)phenyl}-2-[4-{4-methyl-3,4-di(1-tert-butoxyethoxy)phenyl}cyclohexyl]propane corresponding to formula (5m) wherein $R^4$=1-tert-butoxyethyl Purity 98.5%, yield 51.2%

Synthesis Example 19

2-{3,4-di(1-n-butoxyethoxy)phenyl}-2-[4-{4-methyl-3,4-di(1-n-butoxyethoxy)phenyl}cyclohexyl]propane corresponding to formula (5m) wherein $R^4$=1-n-butoxyethyl Purity 98.1%, yield 50.8%

Synthesis Example 20

2-{3,4-di(1-1-butoxyethoxy)phenyl}-2-[4-{4-methyl-3,4-di(1-1-butoxyethoxy)phenyl}cyclohexyl]propane corresponding to formula (5m) wherein $R^4$=i-butoxyethyl Purity 98.1%, yield 48.2%

Synthesis Example 21

2-{3,4-di(dimethoxymethoxy)phenyl}-2-[4-{4-methyl-3,4-di(dimethoxymethoxy)phenyl}cyclohexyl]propane corresponding to formula (5m) wherein $R^4$=dimethoxymethyl Purity 98.2%, yield 73.2%

Synthesis Example 22

2-{3,4-di(diethoxymethoxy)phenyl}-2-[4-{3,4-di(diethoxymethoxy)phenyl-4-methyl}cyclohexyl]propane corresponding to formula (5m) wherein $R^4$=ethoxymethyl Purity 98.8%, yield 81.6%

Synthesis Example 23

2-(3,4-di-tert-butoxyphenyl)-2-{4-(4-methyl-3,4-di-tert-butoxyphenyl)cyclohexyl}propane corresponding to formula (5m) wherein $R^4$=tert-butyl Purity 98.8%, yield 50.2%

Synthesis Example 24

2-(3,4-di-tert-butoxycarbonylmethyloxyphenyl)-2-{4-(4-methyl-3,4-di-tert-butoxycarbonylmethyloxyphenyl)cyclohexyl}propane corresponding to formula (5m) wherein $R^4$=tert-butoxycarbonylmethyl Purity 98.1%, yield 52.8%

Synthesis Example 25

Synthesis of a compound of formula (5m) wherein 33% of $R^4$ is tert-butoxycarbonyl and 67% of $R^4$ is hydrogen In Synthesis Example 15, reaction was carried out as in Synthesis Example 1 except that the amount of di-tert-butyl dicarbonate was changed to 5.8 grams (0.026 mol), yielding a compound of formula (5m) wherein 33% of $R^4$ is tert-butoxycarbonyl group and 67% of $R^4$ is hydrogen atom. The percent replacement was confirmed by NMR analysis. Yield 60.0%.

Synthesis Example 26

Synthesis of a compound of formula (5m) wherein 50% of $R^4$ is tert-butoxycarbonyl and 50% of $R^4$ is hydrogen In Synthesis Example 15, reaction was carried out as in Synthesis Example 1 except that the amount of di-tert-butyl dicarbonate was changed to 8.7 grams (0.040 mol), yielding a compound of formula (5m) wherein 50% of $R^4$ is tert-butoxycarbonyl group and 50% of $R^4$ is hydrogen atom. The percent replacement was confirmed by NMR analysis. Yield 58.6%.

Synthesis Example 27

Synthesis of a compound of formula (5m) wherein 33% of $R^4$ is ethoxyethyl and 67% of $R^4$ is hydrogen In Synthesis Example 16, reaction was carried out as in Synthesis Example 2 except that the amount of ethyl vinyl ether was changed to 6.3 grams (0.088 mol), yielding a compound of formula (5m) wherein 33% of $R^4$ is ethoxyethyl group and 67% of $R^4$ is hydrogen atom. The percent replacement was confirmed by NMR analysis. Yield 59.1%.

Synthesis Example 28

Synthesis of a compound of formula (5m) wherein 50% of $R^4$ is ethoxyethyl and 50% of $R^4$ is hydrogen In Synthesis Example 16, reaction was carried out as in Synthesis Example 2 except that the amount of ethyl vinyl ether was changed to 9.5 grams (0.13 mol), yielding a compound of formula (5m) wherein 50% of $R^4$ is ethoxyethyl group and 50% of $R^4$ is hydrogen atom. The percent replacement was confirmed by NMR analysis. Yield 57.2%.

Dissolution rate regulators comprising novel compounds of Synthesis Examples 1, 2, and 11 to 14 are designated DRI.1 to DRI.6, respectively. Conventional dissolution rate regulators DRI.9 and DRI.10 are for comparison. The molar absorptivity of these dissolution rate regulators was determined from their UV absorption spectrum in methanol solvent at 248 nm. The results are shown in Table 1. For those compounds having phenolic hydroxyl groups partially replaced, the molar absorptivity was calculated from an average molecular weight.

TABLE 1

|  | Dissolution rate regulator | Molar absorptivity (248 nm) |
|---|---|---|
| Synthesis Example | DRI. 1 | 300 |
|  | DRI. 2 | 300 |
|  | DRI. 3 | 290 |
|  | DRI. 4 | 300 |
|  | DRI. 5 | 300 |
|  | DRI. 6 | 320 |
| Comparative Example | DRI. 9 | 5850 |
|  | DRI. 10 | 4500 |

As is evident from Table 1, the dissolution rate regulators according to the invention show significantly reduced light absorption at 248 nm as compared with the conventional dissolution rate regulators.

Examples 1–20 & Comparative Example 1–7

Liquid resist compositions were prepared by dissolving a base resin, a photoacid generator, and a dissolution rate regulator in a solvent in accordance with the formulation shown in Tables 2 and 3. Each of the compositions was passed through a 0.2-$\mu$m Teflon® filter.

The base resins used were a polyhydroxystyrene, designated Polym.1, in which the hydrogen atom of a hydroxyl group was partially protected with a tert-butoxycarbonyl group; a polyhydroxystyrene, designated Polym.2, in which the hydrogen atom of a hydroxyl group was partially protected with a tetrahydrofuranyl group; a polyhydroxystyrene, designated Polym.3, in which the hydrogen atom of a hydroxyl group was partially protected with a 1-ethoxyethyl group; and a polyhydroxystyrene, designated Polym.4, in which the hydrogen atom of a hydroxyl group was partially protected with tert-butoxycarbonyl and 1-ethoxyethyl groups.

The photoacid generators used were PAG.1 to PAG.7, shown below, selected from an onium salt, pyrogallolsulfonic acid derivative, benzylsulfonic acid derivative, bisalkylsulfonyldiazomethane derivative, and N-sulfonyloxyimide derivative.

The dissolution rate regulators used were compounds designated DRR.1 to DRR.10, shown below, selected from 2-(4-hydroxyphenyl)-2-{4-(4-methyl-4-hydroxyphenyl)cyclohexyl}propane in which a phenolic hydroxyl group is replaced by a tert-butoxycarbonyl or 1-ethoxyethyl group in a proportion of 0 to 100%, 2-(3,4-di-tert-butoxycarbonyloxyphenyl)-2-{4-(4-methyl-3,4-di-tert-butoxycarbonyloxyphenyl)cyclohexyl}propane, 1,4-bis[di{4-(tert-butoxycarbonyloxy)-3,5-dimethylphenyl}methyl]benzene, and 1,5-di(tert-butoxycarbonyloxy)-2,4-di(4-tert-butoxycarbonyloxyphenyl)methylbenzene.

The solvents used were propylene glycol monomethyl ether acetate (PGMEA), a 85/15 wt % mixture of ethyl lactate/butyl acetate (EL/BA), and 1-ethoxy-2-propanol (ElPA).

Note that some compositions further contained a nitrogenous compound which was N-methylpyrrolidone (NMP), piperidine-ethanol (PE), and triethanolamine (TEA).

Each liquid resist composition was then spin coated onto a silicon wafer to form a coating of 0.7 $\mu$m thick. With the silicon wafer rested on a hot plate at 100° C., the coating was pre-baked for 120 seconds. The film was exposed to a pattern of light by means of an excimer laser stepper model NSR-2005EX (manufactured by Nikon K.K., numerical aperture NA=0.5), baked at 90° C. for 90 seconds, and developed with an aqueous solution of 2.38% tetramethylammonium hydroxide, obtaining a positive pattern.

The resulting resist pattern was evaluated as follows. First, a sensitivity (Eth value) was determined. Provided that the exposure dose with which the top and bottom of a 0.30-μm line-and-space pattern were resolved at 1:1 was the optimum exposure (sensitivity Eop), the minimum line width of a line-and-space pattern which was recognized separate at this exposure dose was the resolution of a test resist. The configuration of the resist pattern resolved was observed under a scanning electron microscope. It was also observed under a scanning electron microscope whether or not scum generated.

The results are shown in Tables 2 and 3.

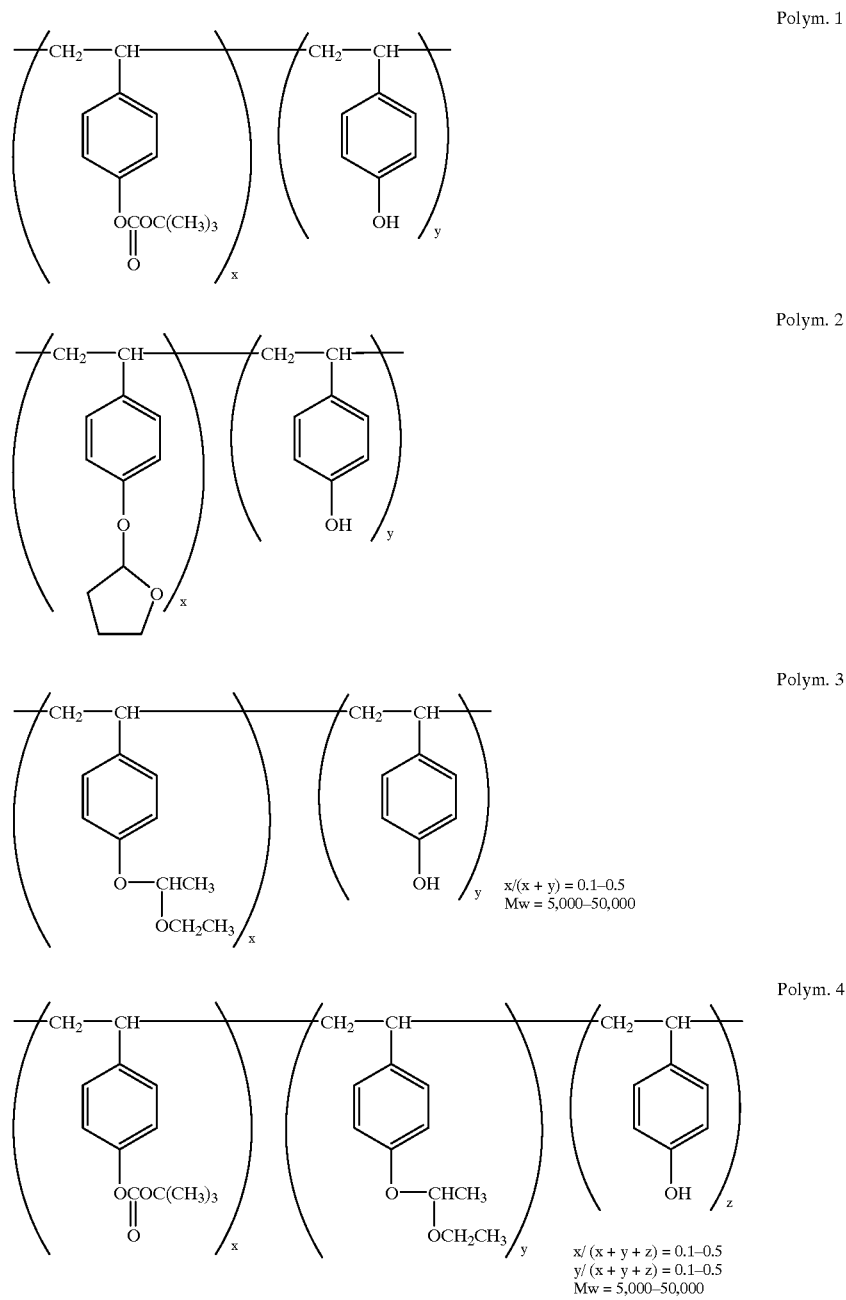

-continued
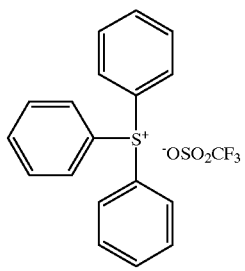
PAG. 1
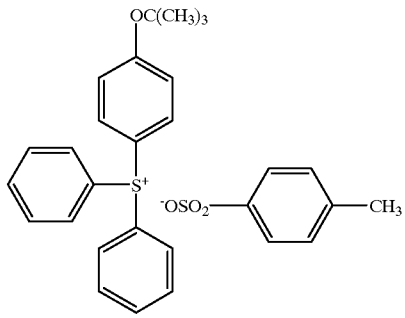
PAG. 2
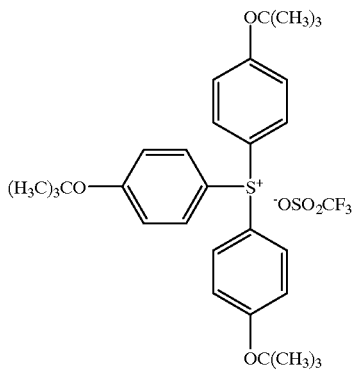
PAG. 3
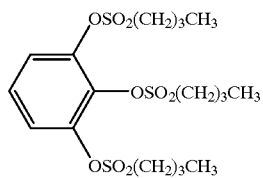
PAG. 4
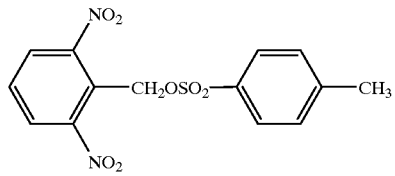
PAG. 5
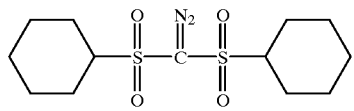
PAG. 6

PAG. 7
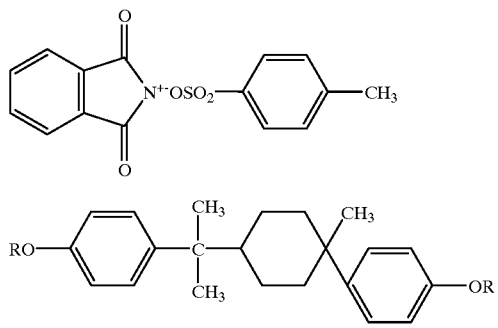
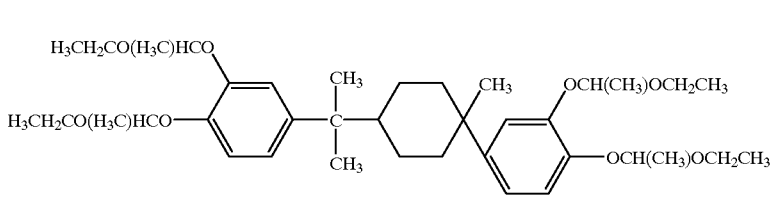
R = —COOC(CH₃)₃ (100%)   DRI. 1
R = —CH(CH₃)OCH₂CH₃ (100%)   DRI. 2
R = —COOC(CH₃)₃ (33%), H(67%)   DRI. 3
R = —COOC(CH₃)₃ (50%), H(50%)   DRI. 4
R = —CH(CH₃)OCH₂CH₃ (33%), H(67%)   DRI. 5
R = —CH(CH₃)OCH₂CH₃ (50%), H(50%)   DRI. 6
R = H (100%)   DRI. 7
DRI. 8
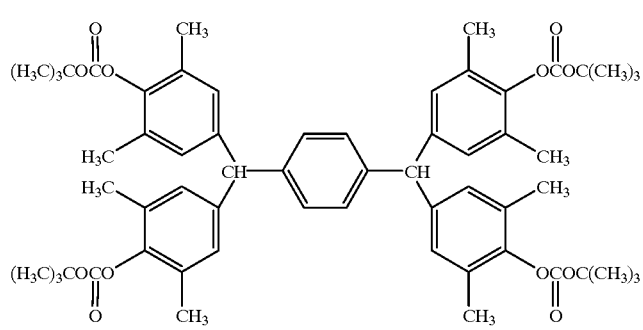
DRI. 9
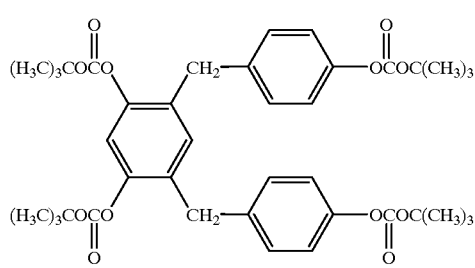
DRI. 10

TABLE 2

| Example | Alkali soluble resin | Photo-acid generator | Dissolution rate regulator | Solvent | Nitrogenous compound | Sensitivity Eop (mJ/cm$^2$) | Resolution ($\mu$m) | Pattern profile |
|---|---|---|---|---|---|---|---|---|
| 1 | Polym. 1 (80) | PAG. 1(5) | DRI. 1(15) | PGMEA (450) | — | 4.5 | 0.24 | rectangular |
| 2 | Polym. 2 (80) | PAG. 2(5) | DRI. 2(15) | PGMEA (450) | — | 3.5 | 0.22 | rectangular |
| 3 | Polym. 3 (80) | PAG. 3(5) | DRI. 8(15) | PGMEA (450) | — | 4.0 | 0.22 | rectangular |
| 4 | Polym. 4 (80) | PAG. 2(1) PAG. 6(4) | DRI. 2(20) | PGMEA (450) | — | 8.5 | 0.24 | rectangular |
| 5 | Polym. 4 (80) | PAG. 2(3) PAG. 5(2) | DRI. 2(20) | PGMEA (450) | — | 4.5 | 0.22 | rectangular |
| 6 | Polym. 4 (80) | PAG. 3(3) PAG. 7(2) | DRI. 2(20) | EL/BA (500) | — | 5.0 | 0.22 | rectangular |
| 7 | Polym. 1 (40) Polym. 2 (40) | PAG. 2(5) | DRI. 2(20) | EL/BA (500) | — | 3.5 | 0.22 | rectangular |
| 8 | Polym. 4 (80) | PAG. 4(3) PAG. 5(2) | DRI. 1(15) | PGMEA (450) | — | 4.0 | 0.22 | rectangular |
| 9 | Polym. 4 (80) | PAG. 2(5) | DRI. 8(15) | PGMEA (450) | — | 5.0 | 0.22 | rectangular |
| 10 | Polym. 4 (80) | PAG. 2(5) | DRI. 5(20) | PGMEA (450) | — | 4.0 | 0.23 | rectangular |
| 11 | Polym. 4 (80) | PAG. 3(5) | DRI. 6(20) | PGMEA (450) | — | 3.5 | 0.24 | rectangular |
| 12 | Polym. 4 (80) | PAG. 2(5) | DRI. 1(15) | EL/BA (500) | NMP (0.1) | 11.0 | 0.22 | rectangular |
| 13 | Polym. 1 (30) Polym. 3 (50) | PAG. 3(5) | DRI. 8(15) | EL/BA (500) | PE (0.96) | 10.5 | 0.20 | rectangular |
| 14 | Polym. 4 (80) | PAG. 2(5) | DRI. 2(15) | PGMEA (450) | TEA (0.06) | 11.0 | 0.20 | rectangular |
| 15 | Polym. 4 (80) | PAG. 2(5) | DRI. 3(10) DRI. 9(10) | PGMEA (450) | — | 8.0 | 0.26 | rectangular |
| 16 | Polym. 4 (80) | PAG. 3(5) | DRI. 4(10) DRI. 9(10) | PGMEA (450) | — | 4.5 | 0.26 | rectangular |
| 17 | Polym. 4 (80) | PAG. 2(5) | DRI. 3(10) DRI. 9(10) | PGMEA (450) | — | 3.5 | 0.26 | rectangular |
| 18 | Polym. 1 (80) | PAG. 2(3) PAG.5 (2) | DRI. 6(10) DRI. 9(10) | EIPA (500) | — | 4.5 | 0.26 | rectangular |
| 19 | Polym. 1 (30) Polym. 2 (50) | PAG.2 (5) | DRI. 6(10) DRI. 10(10) | PGMEA (450) | — | 5.0 | 0.26 | rectangular |
| 20 | Polym. 4 (80) | PAG.3 (3) PAG.5 (2) | DRI. 3(10) DRI. 9(15) | PGMEA (450) | — | 4.0 | 0.26 | rectangular |

TABLE 3

| Comparative Example | Alkali soluble resin | Photo acid generator | Dissolution rate regulator | Solvent | Sensitivity Eop (mJ/cm$^2$) | Resolution ($\mu$m) | Pattern profile |
|---|---|---|---|---|---|---|---|
| 1 | Polym. 4 (80) | PAG. 2(5) | DRI. 9(15) | PGMEA (450) | 4.5 | 0.28 | forward tapered |
| 2 | Polym. 1 (40) Polym. 3 (40) | PAG. 2(1) PAG. 4(4) | DRI. 9(15) | PGMEA (450) | 5.5 | 0.28 | forward tapered |
| 3 | Polym. 4 (80) | PAG. 3(S) | DRI. 10(15) | PGMEA (450) | 4.5 | 0.28 | forward tapered |
| 4 | Polym. 4 (80) | PAG. 2(2) PAG. 7(2) | DRI. 10(15) | EIPA (500) | 4.0 | 0.28 | forward tapered |
| 5 | Polym. 1 (40) | PAG. 4(1) | DRI. 10(15) | EL/BA | 6.0 | 0.28 | forward |

TABLE 3-continued

| | Resist composition (pbw in parentheses) | | | | | | |
|---|---|---|---|---|---|---|---|
| Comparative Example | Alkali soluble resin | Photo acid generator | Dissolution rate regulator | Solvent | Sensitivity Eop (mJ/cm$^2$) | Resolution ($\mu$m) | Pattern profile |
| | Polym. 3 (40) | PAG. 5(4) | | (500) | | | tapered |
| 6 | Polym. 4 (80) | PAG. 2(5) | DRI. 7(10) | PGMEA (450) | 4.0 | 0.28 | forward tapered |
| 7 | Polym. 4 (80) | PAG. 3(1) PAG. 4(4) | DRI. 7(10) | PGMEA (450) | 3.5 | 0.28 | forward tapered |

Japanese Patent Application No. 113197/1996 is incorporated herein by reference.

Although some preferred embodiments have been described, many modifications and variations may be made thereto in the light of the above teachings. It is therefore to be understood that within the scope of the appended claims, the invention may be practiced otherwise than as specifically described.

We claim:

1. A di- or triphenyl monoterpene hydrocarbon derivative of the following general formula (1):

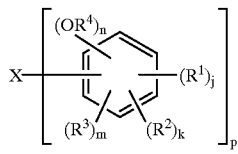
(1)

wherein

X is a divalent or trivalent monoterpene hydrocarbon group, $R^1$ to $R^3$ are independently selected from the group consisting of a hydrogen atom, normal or branched alkyl, normal or branched alkoxy, normal or branched alkoxyalkyl, normal or branched alkenyl, and aryl group, $R^4$ is a hydrogen atom or acid labile group, at least one $R^4$ being an acid labile group, letter n is an integer of 1 to 5, letters j, k and m are integers of 0 to 4 and satisfy n+j+k+m=5, and p is equal to 2 or 3.

2. A mixture of derivatives of formula (1) as set forth in claim 1, 10 to 100 mol % of the entire $R^4$ groups being an acid labile group.

3. The derivative of claim 1 wherein the acid labile group represented by $R^4$ in formula (1) is selected from the group consisting of a group of the following general formula (2a), a silyl group of the following general formula (2b), an acetal group of the following general formula (2c), and a group of the following general formula (2d):

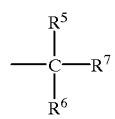
(2a)

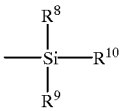
(2b)

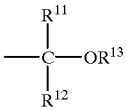
(2c)

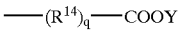
(2d)

wherein $R^5$ to $R^{10}$ are independently selected from the group consisting of a normal or branched alkyl, normal or branched alkoxy, normal or branched alkoxyalkyl, normal or branched alkenyl, and aryl group, which may contain a carbonyl group in their chain, or $R^5$ and $R^6$, and $R^8$ and $R^9$, taken together, may form a ring, $R^{11}$ and $R^{12}$ are independently selected from the group consisting of a hydrogen atom, normal or branched alkyl, normal or branched alkoxy, normal or branched alkoxyalkyl, normal or branched alkenyl, and aryl group, $R^{13}$ is selected from the group consisting of a normal or branched alkyl, normal or branched alkoxyalkyl, normal or branched alkenyl, and aryl group, which may contain a carbonyl group in their chain, or $R^{13}$ may form a ring with $R^{12}$, $R^{14}$ is a divalent aliphatic, alicyclic or aromatic group, Y is an acid labile group, and letter q is equal to 0 or 1.

4. A dissolution rate regulator comprising a derivative according to claim 1.

5. A chemically amplified positive resist composition comprising a dissolution rate regulator according to claim 4.

6. A chemically amplified positive resist composition comprising (A) an organic solvent, (B) an alkali soluble resin, (C) a photoacid generator, and (D) a dissolution rate regulator according to claim 4.

7. A chemically amplified positive resist composition comprising (A) an organic solvent, (B) an alkali soluble resin, (C) a photoacid generator, (D) a dissolution rate regulator according to claim 4, and (E) another dissolution rate regulator.

8. The chemically amplified positive resist composition of claim 6 wherein the alkali soluble resin (B) is a polyhydroxystyrene having a weight-average molecular weight of 3,000 to 100,000 in which the hydrogen atom of some hydroxyl groups is replaced by an acid labile group.

9. A dissolution rate regulator comprising a derivative according to claim 2.

10. A dissolution rate regulator comprising a derivative according to claim 3.

11. A chemically amplified positive resist composition comprising a dissolution rate regulator according to claim 9.

12. A chemically amplified positive resist composition comprising a dissolution rate regulator according to claim 10.

13. A chemically amplified positive resist composition comprising (A) an organic solvent, (B) an alkali soluble resin, (C) a photoacid generator, and (D) a dissolution rate regulator according to claim 9.

14. A chemically amplified positive resist composition comprising (A) an organic solvent, (B) an alkali soluble resin, (C) a photoacid generator, and (D) a dissolution rate regulator according to claim 10.

15. A chemically amplified positive resist composition comprising (A) an organic solvent, (B) an alkali soluble resin, (C) a photoacid generator, and (D) a dissolution rate regulator according to claim 9, and (E) another dissolution rate regulator.

16. A chemically amplified positive resist composition comprising (A) an organic solvent, (B) an alkali soluble resin, (C) a photoacid generator, and (D) a dissolution rate regulator according to claim 10, and (E) another dissolution rate regulator.

17. The chemically amplified positive resist composition of claim 13 wherein the alkali soluble resin (B) is a polyhydroxystyrene having a weight-average molecular weight of 3,000 to 100,000 in which the hydrogen atom of some hydroxyl groups is replaced by an acid labile group.

18. The chemically amplified positive resist composition of claim 14 wherein the alkali soluble resin (B) is a polyhydroxystyrene having a weight-average molecular weight of 3,000 to 100,000 in which the hydrogen atom of some hydroxyl groups is replaced by an acid labile group.

19. The chemically amplified positive resist composition of claim 7 wherein the alkali soluble resin (B) is a polyhydroxystyrene having a weight-average molecular weight of 3,000 to 100,000 in which the hydrogen atom of some hydroxyl groups is replaced by an acid labile group.

20. The chemically amplified positive resist composition of claim 15 wherein the alkali soluble resin (B) is a polyhydroxystyrene having a weight-average molecular weight of 3,000 to 100,000 in which the hydrogen atom of some hydroxyl groups is replaced by an acid labile group.

21. The chemically amplified positive resist composition of claim 16 wherein the alkali soluble resin (B) is a polyhydroxystyrene having a weight-average molecular weight of 3,000 to 100,000 in which the hydrogen atom of some hydroxyl groups is replaced by an acid labile group.

22. A derivative of claim 1, wherein X is a non-cyclic or monocyclic di- or trivalent monoterpene hydrocarbon group.

23. A derivative of claim 1, wherein X is a myrcene, ocimene, geraniol, nerol, limonene, terpinene, sylvestrene or phellandrene di- or trivalent nonoterpene hydrocarbon group.

24. A derivative of claim 1 which is selected from the group consisting of compounds of the following general formulae (4a) to (4d):

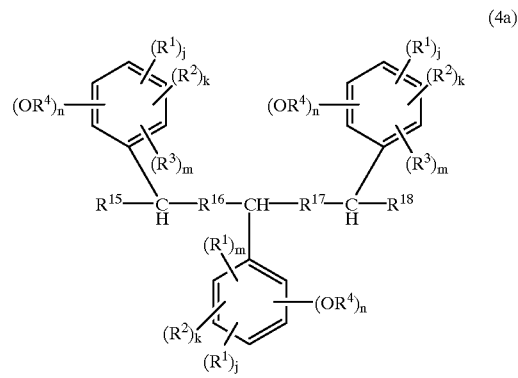

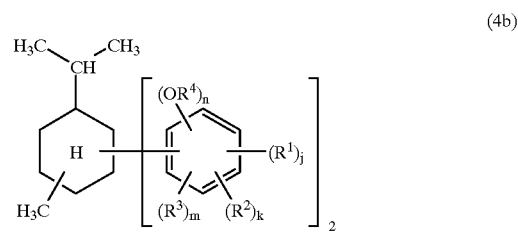

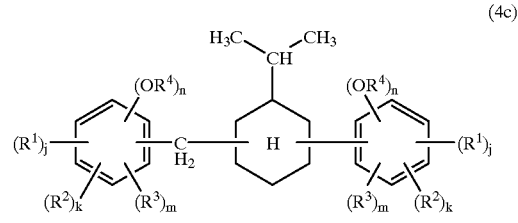

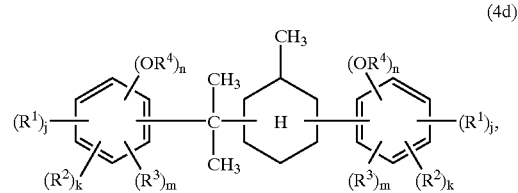

wherein $R^{15}$ and $R^{18}$ each are a normal or branched alkyl group and $R^{16}$ and $R^{17}$ each are a normal or branched alkylene group while the total number of carbon atoms in $R^{15}$ to $R^{18}$ is 7, and $R^1$, $R^2$, $R^3$, $R^4$, n, j, k and m have the meanings set forth in claim 1.

25. A derivative of claim 1 which is selected from the group consisting of compounds of the following formulae (5a) to (5o):

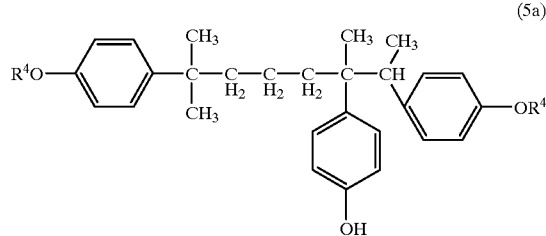
(5a)
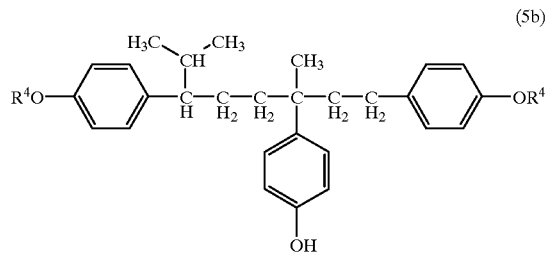
(5b)
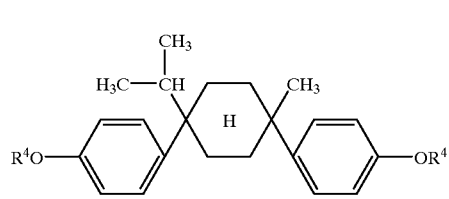
(5c)
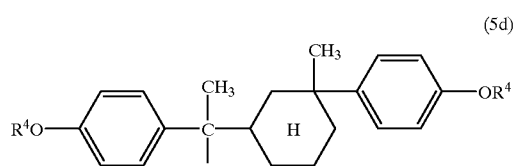
(5d)
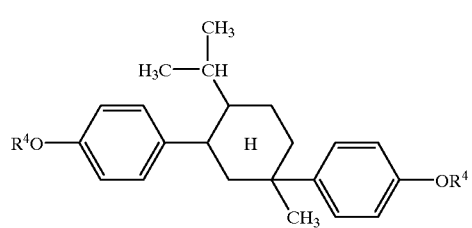
(5e)
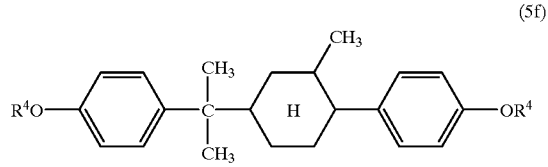
(5f)
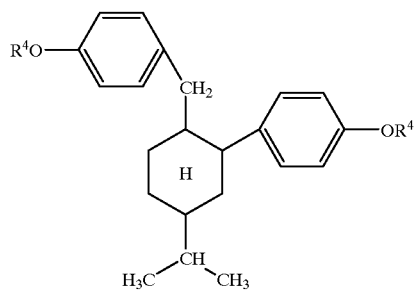
(5g)
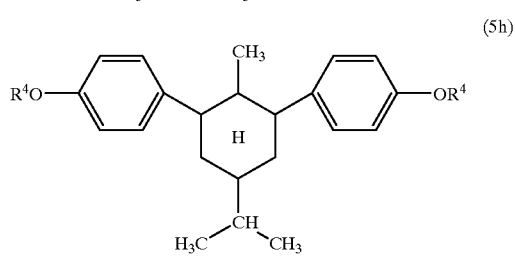
(5h)
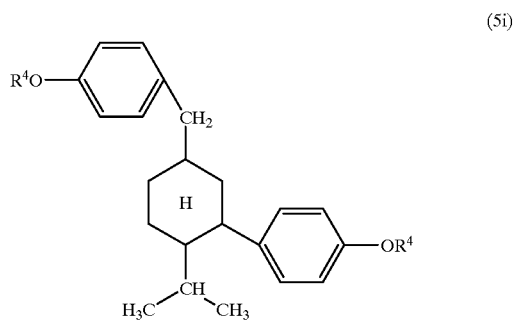
(5i)
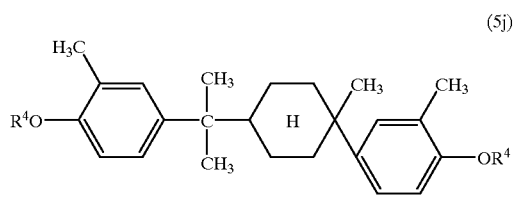
(5j)
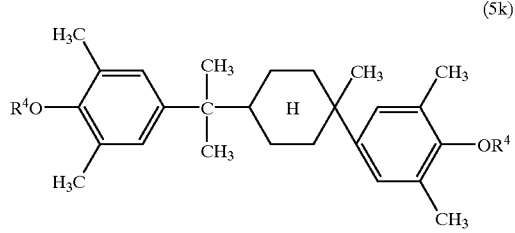
(5k)
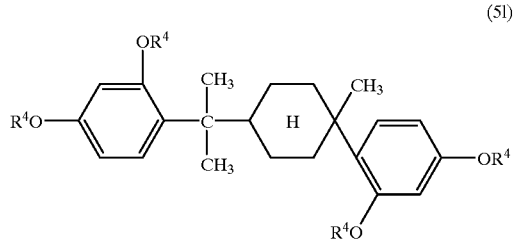
(5l)

-continued

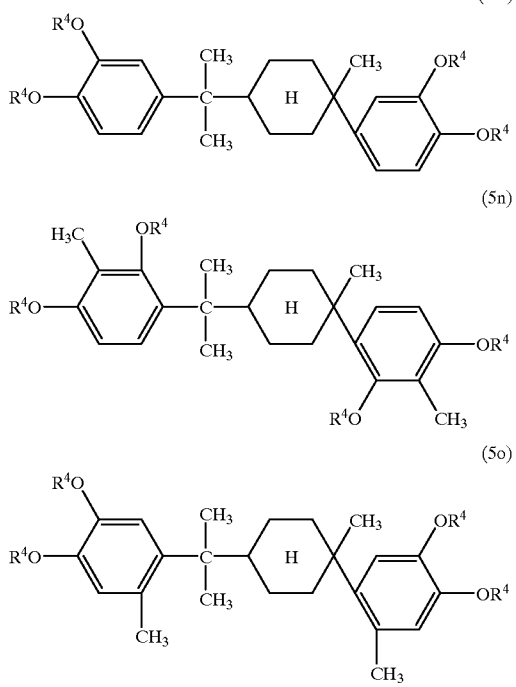

wherein R$^4$ has the meaning set forth in claim 1.

26. A chemically amplified positive resist composition according to claim 6, wherein the photoacid generator (C) is an onium salt of the formula (13):

$$(R)_rMA \qquad (13)$$

wherein the R groups, which may be identical or different, are substituted or unsubstituted aromatic groups; M is sulfonium or iodonium; A is p-toluenesulfonate, trifluoromethanesulfonate, nonafluorobutanesulfonate, butanesulfonate or a normal, branched or cyclic alkylsulfonate having 1–20 carbon atoms; and r is 2 or 3.

27. A chemically amplified positive resist composition according to claim 7, wherein the photoacid generator (C) is an onium salt of the formula (13):

$$(R)_rMA \qquad (13)$$

wherein the R groups, which may be identical or different, are substituted or unsubstituted aromatic groups; M is sulfonium or iodonium; A is p-toluenesulfonate, trifluoromethanesulfonate, nonafluorobutanesulfonate, butanesulfonate or a normal, branched or cyclic alkylsulfonate having 1–20 carbon atoms; and r is 2 or 3.

28. A chemically amplified positive resist composition according to claim 6, which contains, by weight, 150 to 700 parts of organic solvent (A), 70 to 90 parts of alkali soluble resin (B), 0.5 to 15 parts of photoacid generator (C) and 1 to 40 parts of dissolution rate regulator (D).

29. A chemically amplified positive resist composition according to claim 7, which contains, by weight, 150 to 700 parts of organic solvent (A), 70 to 90 parts of alkali soluble resin (B), 0.5 to 15 parts of photoacid generator (C), 1 to 40 parts of dissolution rate regulator (D) and 1 to 40 parts of the other dissolution rate regulator (E).

30. A chemically amplified positive resist composition according to claim 7, wherein the other dissolution rate regulator (E) is a bisphenol-A or polyphenol derivative having a hydrogen atom of a hydroxyl group replaced by a tert-butyl derivative substituent, a normal or branched chain acetal group or a cyclic acetal group.

* * * * *